US008409639B2

(12) United States Patent
Lewis et al.

(10) Patent No.: US 8,409,639 B2
(45) Date of Patent: Apr. 2, 2013

(54) METHODS AND SYSTEMS FOR PRODUCING ETHANOL USING RAW STARCH AND FRACTIONATION

(75) Inventors: Stephen M. Lewis, Sioux Falls, SD (US); Shon Erron Van Hulzen, Brandon, SD (US)

(73) Assignee: Poet Research, Inc., Sioux Falls, SD (US)

( * ) Notice: Subject to any disclaimer, the term of this patent is extended or adjusted under 35 U.S.C. 154(b) by 0 days.

(21) Appl. No.: 12/944,618

(22) Filed: Nov. 11, 2010

(65) Prior Publication Data
US 2011/0111085 A1 May 12, 2011

Related U.S. Application Data

(63) Continuation of application No. 11/682,195, filed on Mar. 5, 2007, which is a continuation of application No. 11/077,969, filed on Mar. 10, 2005, now abandoned, which is a continuation-in-part of application No. 10/798,226, filed on Mar. 10, 2004, now abandoned.

(60) Provisional application No. 60/453,442, filed on Mar. 10, 2003, provisional application No. 60/614,916, filed on Sep. 30, 2004, provisional application No. 60/615,155, filed on Oct. 1, 2004, provisional application No. 60/552,108, filed on Mar. 10, 2004.

(51) Int. Cl.
*C12Q 1/54* (2006.01)
*C12Q 1/02* (2006.01)
*A23F 3/16* (2006.01)
*C12P 7/06* (2006.01)
*C12P 19/20* (2006.01)
*C12Q 1/34* (2006.01)
*C12Q 1/40* (2006.01)

(52) U.S. Cl. ............... 426/11; 426/52; 435/14; 435/18; 435/22; 435/29; 435/96; 435/161

(58) Field of Classification Search .................... 426/11, 426/52; 435/14, 18, 22, 29, 96, 161
See application file for complete search history.

(56) References Cited

U.S. PATENT DOCUMENTS

| 2,440,925 | A | 5/1948 | Boeckeler |
|---|---|---|---|
| 3,940,492 | A | 2/1976 | Ehnstrom |
| 4,009,074 | A | 2/1977 | Walon |
| 4,092,434 | A | 5/1978 | Yoshizumi et al. |
| 4,243,750 | A | 1/1981 | Muller et al. |
| 4,279,747 | A | 7/1981 | Chen |
| 4,287,303 | A | 9/1981 | Dahlberg et al. |
| 4,309,254 | A | 1/1982 | Dahlstrom et al. |
| 4,316,956 | A | 2/1982 | Lutzen |
| 4,358,536 | A | 11/1982 | Thorsson et al. |
| 4,361,651 | A | 11/1982 | Keim |
| 4,376,163 | A | 3/1983 | Ehnstrom |
| 4,460,687 | A | 7/1984 | Ehnstrom |
| 4,474,883 | A | 10/1984 | Yamamoto et al. |
| 4,490,469 | A | 12/1984 | Kirby et al. |
| 4,514,496 | A | 4/1985 | Yoshizumi et al. |
| 4,522,920 | A | 6/1985 | Thorsson et al. |
| 4,540,663 | A | 9/1985 | Witt |
| 4,591,560 | A | 5/1986 | Kainuma et al. |
| 4,618,579 | A | 10/1986 | Dwiggins et al. |
| 4,716,218 | A | 12/1987 | Chen et al. |
| 4,727,026 | A | 2/1988 | Sawada et al. |
| 4,760,025 | A | 7/1988 | Estell et al. |
| 4,863,864 | A | 9/1989 | Ashikari et al. |
| 4,876,196 | A | 10/1989 | Salzbrunn et al. |
| 4,933,279 | A | 6/1990 | Carroll et al. |
| 5,061,497 | A | 10/1991 | Thacker et al. |
| 5,084,385 | A | 1/1992 | Ashikari et al. |
| 5,087,417 | A | 2/1992 | Dumbroff et al. |
| 5,177,008 | A | 1/1993 | Kampen |
| 5,177,009 | A | 1/1993 | Kampen |
| 5,180,669 | A | 1/1993 | Antrim |
| 5,231,017 | A | 7/1993 | Lantero et al. |
| 5,250,182 | A | 10/1993 | Bento et al. |
| 5,260,089 | A | 11/1993 | Thornberg |
| RE34,606 | E | 5/1994 | Estell et al. |
| 5,322,778 | A | 6/1994 | Antrim et al. |
| 5,364,770 | A | 11/1994 | Berka et al. |
| 5,545,543 | A | 8/1996 | Zinnamosca et al. |
| 5,559,031 | A | 9/1996 | Zinnamosca et al. |
| 5,652,127 | A | 7/1997 | Mitchinson et al. |
| 5,688,674 | A | 11/1997 | Choi et al. |
| 5,721,127 | A | 2/1998 | Deweer et al. |
| 5,721,128 | A | 2/1998 | Deweer et al. |
| 5,736,375 | A | 4/1998 | Deweer et al. |

(Continued)

FOREIGN PATENT DOCUMENTS

| CA | 1143677 | 3/1983 |
|---|---|---|
| DE | 267508 | 5/1989 |

(Continued)

OTHER PUBLICATIONS

Gulati et al. 1996. Assessment of Ethanol Production Options for Corn Products. Bioresource Technology, vol. 58, pp. 253-264.*
Nigam et al. 1995. Enzyme and microbial systems involved in starch processing. Enzyme and Microbial Technology, vol. 17, pp. 770-778.*
U.S. Appl. No. 12/716,989, filed Mar. 3, 2010, Kwiatkowski.
U.S. Appl. No. 12/886,483, filed Sep. 20, 2010, Lewis et al.
U.S. Appl. No. 12/944,606, filed Nov. 11, 2010, Lewis et al.

(Continued)

*Primary Examiner* — Jon P Weber
*Assistant Examiner* — Kailash C Srivastava
(74) *Attorney, Agent, or Firm* — Foley & Lardner LLP

(57) ABSTRACT

The present invention relates to methods for producing high levels of alcohol during fermentation of plant material, and to the high alcohol beer produced. The method can include fractionating the plant material. The present invention also relates to methods for producing high protein distiller's dried grain from fermentation of plant material, and to the high protein distiller's dried grain produced. The method can include drying a co-product by ring drying, flash drying, or fluid bed drying. The present invention further relates to reduced stack emissions from drying distillation products from the production of ethanol.

17 Claims, 4 Drawing Sheets

U.S. PATENT DOCUMENTS

| | | | |
|---|---|---|---|
| 5,736,499 | A | 4/1998 | Mitchinson et al. |
| 5,756,714 | A | 5/1998 | Antrim et al. |
| 5,817,498 | A | 10/1998 | Deweer et al. |
| 5,824,532 | A | 10/1998 | Barnett et al. |
| 5,849,549 | A | 12/1998 | Barnett et al. |
| 5,958,739 | A | 9/1999 | Mitchinson et al. |
| 5,981,237 | A | 11/1999 | Meagher et al. |
| 6,074,854 | A | 6/2000 | Deweer et al. |
| 6,136,576 | A | 10/2000 | Diaz-Torres et al. |
| 6,171,817 | B1 | 1/2001 | Berka et al. |
| 6,228,177 | B1 | 5/2001 | Torget |
| 6,313,328 | B1 | 11/2001 | Ulrich et al. |
| 6,423,145 | B1 | 7/2002 | Nguyen et al. |
| 6,451,063 | B1 | 9/2002 | Clarkson et al. |
| 6,509,180 | B1 | 1/2003 | Verser et al. |
| 6,538,182 | B1 | 3/2003 | Thompson et al. |
| 6,616,948 | B2 | 9/2003 | Gustavsson et al. |
| 6,664,095 | B1 | 12/2003 | Suryanarayan et al. |
| 6,709,527 | B1 | 3/2004 | Fechter et al. |
| 6,774,284 | B1 | 8/2004 | Thompson et al. |
| 6,803,218 | B1 | 10/2004 | Seyfried et al. |
| 6,849,439 | B2 | 2/2005 | Henson et al. |
| 6,849,782 | B2 | 2/2005 | Thompson et al. |
| 6,855,529 | B2 | 2/2005 | Thompson et al. |
| 6,867,237 | B1 | 3/2005 | Taylor et al. |
| 6,878,860 | B1 | 4/2005 | Thompson et al. |
| 7,344,876 | B2 | 3/2008 | Levine |
| 7,579,177 | B2 | 8/2009 | Olsen et al. |
| 7,622,284 | B2 | 11/2009 | Op Den Camp et al. |
| 2003/0134395 | A1 | 7/2003 | Shetty et al. |
| 2003/0134396 | A1 | 7/2003 | Shetty et al. |
| 2003/0180900 | A1 | 9/2003 | Lanteo |
| 2003/0203454 | A1 | 10/2003 | Chotani et al. |
| 2004/0023349 | A1 | 2/2004 | Bisgaard-Frantzen et al. |
| 2004/0043117 | A1 | 3/2004 | Cope et al. |
| 2004/0063184 | A1 | 4/2004 | Grichko |
| 2004/0080923 | A1 | 4/2004 | Janisch |
| 2004/0091983 | A1 | 5/2004 | Veit et al. |
| 2004/0115779 | A1 | 6/2004 | Olsen et al. |
| 2004/0157301 | A1 | 8/2004 | Chotani et al. |
| 2004/0192896 | A1 | 9/2004 | Finch |
| 2004/0197409 | A1 | 10/2004 | Iyer et al. |
| 2004/0219649 | A1 | 11/2004 | Olsen et al. |
| 2004/0234649 | A1 | 11/2004 | Lewis et al. |
| 2005/0026261 | A1 | 2/2005 | Otto et al. |
| 2005/0042737 | A1 | 2/2005 | Vikso-Nielsen et al. |
| 2005/0100996 | A1 | 5/2005 | Lantero, Jr. et al. |
| 2005/0136525 | A1 | 6/2005 | Baldwin et al. |
| 2005/0208623 | A1 | 9/2005 | Baldwin et al. |
| 2005/0233030 | A1 | 10/2005 | Lewis et al. |
| 2005/0239181 | A1 | 10/2005 | Lewis et al. |
| 2006/0051847 | A1 | 3/2006 | Gunnarsson et al. |
| 2006/0246563 | A1 | 11/2006 | Eroma et al. |
| 2007/0178567 | A1 | 8/2007 | Lewis |
| 2007/0196907 | A1 | 8/2007 | Lewis |
| 2007/0202214 | A1 | 8/2007 | Lewis et al. |
| 2008/0032373 | A1 | 2/2008 | Bhargava |
| 2009/0053793 | A1 | 2/2009 | Lefebvre et al. |
| 2010/0041116 | A1 | 2/2010 | Lewis et al. |
| 2010/0151549 | A1 | 6/2010 | Bhargava |
| 2010/0196980 | A1 | 8/2010 | Smith et al. |
| 2010/0227369 | A1 | 9/2010 | Narendranath |
| 2010/0233771 | A1 | 9/2010 | McDonald |
| 2011/0250312 | A1 | 10/2011 | Lewis |

FOREIGN PATENT DOCUMENTS

| | | |
|---|---|---|
| EP | 0138428 | 4/1985 |
| EP | 0 140 410 | 5/1985 |
| EP | 0 171 218 | 2/1986 |
| GB | 2089836 | 12/1981 |
| JP | 58-005145 | 1/1983 |
| JP | 59-179093 | 10/1984 |
| RU | 2001103 | 10/1993 |
| RU | 2127760 | 3/1999 |
| WO | WO 91/03543 | 3/1991 |
| WO | WO 92/20777 | 11/1992 |
| WO | WO 95/13362 | 5/1995 |
| WO | WO 97/27047 | 7/1997 |
| WO | WO 02/38787 | 5/2002 |
| WO | WO 02/074895 | 9/2002 |
| WO | WO 03/018766 | 3/2003 |
| WO | WO 03/062430 | 7/2003 |
| WO | WO03/066816 | 8/2003 |
| WO | WO 03/066826 | 8/2003 |
| WO | WO 03/068976 | 8/2003 |
| WO | WO-2004/080923 A2 | 9/2004 |
| WO | WO 2004/081193 | 9/2004 |
| WO | WO-2004/106533 A1 | 12/2004 |
| WO | WO 2005/052148 | 6/2005 |
| WO | WO 2005/082155 | 9/2005 |

OTHER PUBLICATIONS

Abouzied, et al., Direct fermentation of potato starch to ethanol by cocultures of *Aspergillus niger* and *Saccharomyces cerevisiae*, Appl Environ Microbiol, 1986, 52(5):1055-9.

Aden et al., 2002, Lignocelluloisic Biomass to Ethanol Process Design and Economics Utilizing Co-Current Dilute Acid Prehydrolysis and Enzymatic Hydrolysis for Corn Stover. NREL Report, pp. 1-88 and Appendices A-G.

Aldrich, "New Enzymes Lower Ethanol Production Fuel Costs", BridgeNews, Kansas City, Apr. 4, 2004.

Allison et al., "Transformation of the thermophillic fungus *Humicola grisea* var. *thermoidea* and overproduction of *Humicola* glucoamylase", Curr Genet (1992) 21:225-229.

Argus Leader.Com., Web Page—Business—Broin Goes to Court, Printed Jun. 27, 2006. pp. 1-3.

Ashikari et al., "*Rhizopus* Raw-Starch-Degrading Glucoamylase: Its Cloning and Expression in Yeast". Agric. Bio. Chem. 50(4), 957-964 (1986).

Author Unknown "Alcohol and Alcohol Derivative" (Internet Mar. 2003).

Author Unknown "Chapter 1. Review of the Literature—Coproducts and Near Coproducts of Fuel Ethanol Fermentation from Grain", *Agriculture and Agri-Food Canada Research Branch*(Internet Mar. 2003).

Author Unknown "Determination of acid or—Amylase activity, FIA", SOP No. EB-SM-0259.01/01 pp. 1-14 (Internet Mar. 2003).

Author Unknown "Determination of Amyloglucosidase Activity using the Auto Analyzer", Novozymes Analytical Method EB-SM-0131.02/01 (Internet Mar. 2003).

Author Unknown "Enzymatic modification of starch granules: peeling off versus porosity", TNO Nutrition and Food Research, Dec. 28, 2000, pp. 1-2.

Author Unknown "Ethanol Fuels: The Clean Breeze".

Author Unknown "Grain Processing Enzymes for Sweetener Production", Genencor International. Apr. 2004, pp. 1-3.

Author Unknown "Novelose" Resistant Starch—The starch that thinks it's a fiber, National Starch and Chemical Compnay, 2003.

Author Unknown "Nutrient composiiton of DDGS (100% dry matter basis) from various reference—Table 1", Distillers Grains Quarterly, First Quarter 2006, pp. 27-28.

Author Unknown "Ready for Research", BioFuels Journal, pp. 20-23 (4Q04). Bothast, "Ethanol research facility one of a kind", Industrial Oil Products Article, vol. 15(8):518-519 (Aug. 2004).

Author Unknown "Resistant starch: the new generation of fiber," Functional Foods & Nutraceuticals, Sep./Oct. pp. 20-22.

Author Unknown "SIU Edwardsville National Corn to Ethanol Research Pilot Plant Process Description", Project No. 24307-78188, Washington group Nov. 12, 2001.

Author Unknown "Spirizyme Plus for ethanol production", Novozymes Application Sheet Ethanol/2002-03379-03.pdf (Internet Mar. 2003).

Author Unknown "Very High Gravity Technology", Ethanol Producer Magazine, Jan. 2006.

Bardini, G. et al., "Continuous clarification of grape must by flotation," Vini d'italia, vol. 34, No. 1 pp. 31-38 (1992)(1 page Abstract).

Barr-Rosin, "Fluidised Bed Dryers and Coolers." GEA. www.barr-rosin.com/english/pdf/fluid.pdf.

Belya et al., "Composition of corn and distillers dried grains with solubles from dry grind ethanol processing", Bioresource Technology 94 (2004) 293-298.

Berven, "The Making of Broin Project X", Ethanol Producer Magazine, Feb. 2005, pp. 66-71.
Biotimes: The enzyme e-zine, "Fuel Ethanol Products" (Jan. 2003).
Biswas et al., "Analysis of Headspace Compounds of Distillers Grains using SPME in Conjunction with GC/MS and TGA", Journal of Cereal Science, 33(2001) 223-229.
Boel et al., "Glucoamylases G1 and G2 from *Aspergillus niger* are synthesized from two different but closely related mRNAs", The EMBP Journal, vol. 3, No. 5 pp. 1097-1102 (1984).
Bothast, "Ethanol research facility one of a kind," Industrial Oil Products Article, vol. 15(8):518-519 (Aug. 2004).
Brown et al., "The effect of temperature on the ehtanol tolerance of the yeast, *Saccharomyces uvarum*", Biotechnology Letters, vol. 4, 269-274 (1982).
Bryan, "Changing the Game", Ethanol Producer Magazine, pp. 58-63 (Aug. 2005).
Carlson, M., "Distillers ByProducts for Swine Diets", Missouri Value Added Development Center (Internet Mar. 2003).
Casey et al., "Reevaluation of Alcohol Synthesis and Tolerance on Brewer's Yeast", American Society of Brewing Chemists, Inc., vol. 43, No. 2, pp. 75-83 (1985).
Chen et al., "Comparison of four different chemical pretreatments of corn stover for enhancing enzymatic digestibility." Biomass and Bioenergy, vol. 33, Jun. 26, 2009. pp. 1381-1385.
Chen et al., "Effect of replacing helical glycine residues with alanines on reversible and irreversible stability and production of *Aspergillus awamori* glucoamylase", Protein Engineering, vol. 9, No. 6, pp. 499-505 (1996).
Chi Z.M.; Liu Z. R., "High-concentration alcoholic production from hydrolysate of raw ground corn by a tetraploid yeast strain" Biotechnolgy Letters, vol. 15 No. 8, Aug. 31, 1993, pp. 877-882.
Civil Docket Sheet for Case No. 04-ev-4202 printed Jun. 23, 2006.
International Search Report dated Jun. 1, 2005.
International Search Report mailed Dec. 9, 2005.
International Search Report mailed Sep. 15, 2006.
PCT2005US008155 Internation Search Report Dated Nov. 30, 2005 and Written Opinion.
Daugulis et al., "The Economics of Ethanol Production by Extractive Fermentation", The Canadian J. of Chemical Engineering, vol. 69, pp. 48-497 (Apr. 1991).
Dettori-Campus et al., "Hydrolysis of Starch Granules by the Amyase from *Bacillus stearothermophilus* NCA 26", Process Biochemistry, 27 (1992) 17-21.
Dewitt-Dick et al., "A chemical free method of microbiological control in recirculating cooling water systems".
District Court Civil Docket No. 1: Complaint, filed by Broin and Associates, Inc., Entered: Dec. 15, 2004.
District Court Civil Docket No. 102: Genencor's Notice to Take Deposition of Novozymes North America, Inc., Entered May 2, 2005.
District Court Civil Docket No. 112: Transcript of Proceedings held on Mar. 4, 2005 regarding Docket No. 69, motion Hearing, Entered: May 13, 2005.
District Court Civil Docket No. 132: Memorandum Opinion and Order regarding Docket No. 54, denying in part Motion to Dismiss as to Counts III, IV, V, and VIII and granting without prejudice to Plaintiff's right to amend as to Counts VI and VII, denying Docket No. 54, Motion for a more Definite Statement Signed by Judge Lawrence L. Piersol on Jul. 26, 2005, Entered: Jul. 26, 2005.
District Court Civil Docket No. 138: Genencor International, Inc.'s Answer to Amended Complaint and Counterclaim against Broin end Associates, Inc., by Genencor International, Inc. Entered: Aug. 29, 2005.
District Court Civil Docket No. 148: Reply to Docket No. 138, Answer to Amended Complaint and Counterclaim against filed by Broin and Associates, Inc., Broin and Associates, Inc. Entered: Sep. 20, 2005.
District Court Civil Docket No. 15-1: First Amended Complaint, filed by Broin and Associates, Inc. (Attachments: #1 Exhibit A—Press Release #2 Exhibit B—Magazine Article), Entered Jan. 25, 2005.
District Court Civil Docket No. 15-2: Press Release dated Nov. 4, 2004, Broin Companies Announces Ethanol Technology Revolution.
District Court Civil Docket No. 153: Memorandum in Support regarding Docket No. 152, Motion to dismiss First Amended Complaint Based on International Violations of Protective Order filed by Genencor International, Inc. (Sanford, Steven) (Entered: Sep. 30, 2005).
District Court Civil Docket No. 16: First Motion to Expedite Discovery and Supporting Brief by Broin and Associates, Inc., Entered: Jan. 25, 2005.
District Court Civil Docket No. 17-1: Declaration of Jeffrey C. Brown regarding (16) First Motion to Expedite Discovery and Supporting Brief, Entered: Jan. 25, 2005.
District Court Civil Docket No. 17-6: Exhibit E of Docket No. 17, Plaintiff's First Set of Interrogatories to Defendant, Entered: Jan. 25, 2005.
District Court Civil Docket No. 50-1: Affidavit of Steven W. Sanford in Support of Defendant Genencor's Opposition to Motion for Summary Judgment, Entered Feb. 14, 2005.
District Court Civil Docket No. 50-6: Exhibit D of Docket No. 50, Jan. 10, 2005 letter from Mark Skoog to Ben Brown, Entered: Feb. 14, 2005.
District Court Civil Docket No. 52: Memorandum in Opposition regarding Docket No. 16, First Motion to Expedite Discovery and Supporting Brief, filed by Genencor International, Inc., Entered: Feb. 14, 2005.
District Court Civil Docket No. 53: Motion for Discovery, Requiring Plaintiff to Specify Trade Secrets Prior to Commencement of Discovery and Supporting Brief, b y Genencor International, Inc. Entered: Feb. 14, 2005.
District Court Civil Docket No. 54: Motion to Dismiss Pursuant to FRCP 12(b)(6): Motion for a More Definite Statement Pursuant to FRCP 12(e) and Supporting Brief, by Genencor International, Inc., Entered: Feb. 14, 2005.
District Court Civil Docket No. 61: Response to Motion regarding Docket No. 53, Motion for Discovery, Requiring Plaintiff to Specify Trade Secrets Prior to Commencement of Discovery and Supporting Brief, filed by Broin and Associates, Inc., Entered: Feb. 28, 2005.
District Court Civil Docket No. 62: Reply to Motion Response regarding Docket No. 16, First Motion to Expedite Discovery and Supporting Brief, filed by Broin and Associates, Inc., Entered: Mar. 1, 2005.
District Court Civil Docket No. 67: Reply to Motion Response regarding Docket No. 53, Motion for Discovery, Requiring Plaintiff to Specify Trade Secrets Prior to Commencement of Discovery and Supporting Brief, filed by Genencor International, Inc. Entered: Mar. 2, 2005.
District Court Civil Docket No. 68: Form 35 Report of parties Planning Meeting and Scheduling Information, Entered: Mar. 3, 2005.
District Court Civil Docket No. 77: Memorandum in Opposition regarding Docket No. 54, Motion to Dismiss Pursuant to FRCP 12(b)(6): Motion for a More Definite Statement Pursuant to FRCP 12(e) and Supporting Brief, filed by Broin and Associates, inc. Entered: Mar. 9, 2005.
District Court Civil Docket No. 85: Reply to Motion Response regarding Docket No. 54, Motion to Dismiss Pursuant to FRCP 12(b0(6): Motion for a More Definite Statement Pursuant to FRCP 12(e) and Supporting Brief, filed by Genencor International, Inc., Entered: Mar. 23, 2005.
District Court Civil Docket No. 90: Response to Docket No. 87 Brief, Regarding Genencor's Objections to Broin's Identification of Trade Secrets, filed by Broin and Associates, inc., Entered: Apr. 11, 2005.
District Court Civil Docket No. 95: Form 35 Report of Parties Planning Meeting and Scheduling information, Entered: Apr. 18, 2005.
Dong, F.M. et al., "The Neutral Detergent Fiber, Acid Detergent Fiber, Crude Fiber, and Lignin Contents of Distillers' Dried Grains with Solubles," Journal of Food Science, vol. 52, No. 2, pp. 403-405, 1987.
Donohoe et al., "Detecting cellulose penetration into corn stover and cell walls by immuno-electron microscopy," Biotechnology and Bioengineering, vol. 103, Feb. 11, 2009, pp. 480-489.
Dunn-Coleman et al., "Production of granular starch hydrolyzing enzymes for low energy grain ethanol production", 27th Symposium on Biotechnology for Fuels and Chemicals, Genencor Presentation (May 2005).

Elander et al., "Summary of findings from the Biomass Refining Consortium for Applied Fundamentals and Innovation (CAFI): corn stover pretreatment" Cellulose, vol. 16, Jun. 26, 2009, pp. 649-659.

Farid, M. et al., "Alcohol production from starch by mixed cultures of *Aspergillus awamori* and immobilized *Saccharomyces cerevisiae* a different agitation speeds", J. Basic Microbio, 42(3):162-71 (2002) (Abstract only).

Form PCT/ISA/206 and Annex to Form PCT/ISA/206, Invitation to Pay Additional Fees and Partial International Search for International Patent Application PCT/US2006/017041, dated Sep. 15, 2006.

Form PCT/ISA/220, International Search Report and Written Opinion of International Patent Application PCT/US2005/008156, dated Mar. 7, 2006.

Fox, B. (1997) in Fermentation and Biomedical Engineering Handbook Principles, Process Design, and Equipment, Second Edition, Vogel et al (eds.). Noyea Publications, WasWood, Nlw Icrs V-07675, p. 734-758.

Fujio et al., "Alcohol Fermentation of Raw Cassava Starch by *Rhizopus koji* without cooking."

Fujio et al., "Ethanol Fermentation of Raw Cassava Starch with *Rhizopus koji* in a Gas Circulation Type Fermentor", Biotechnology and Bioengineering, vol. 27:1270-1273, Aug. 1985.

GCOR Lantero patent application search USPTO site.May 17, 2005.

Genencor Inventor Search, Oct. 3, 2005.

Hamdy et al., "Effects of virginiamycin on Fermentation Rate by Yeast", Biomass and Bioenergy, vol. 11, No. 1 pp. 1-9 (1996).

Hamelinck et al. "Ethanol from lignocellulosic biomass: techno-economic performance in short-, middle- and long term" Biomass and Bioenergy, vol. 28, 2005, pp. 384-410.

Han et al. (1987). Amylolysis of Raw Corn by *Aspergillus niger* for Simultaneous Ethanol Fermentation, Biotechnology and Bioengineering, vol. 30, pp. 225-232.

Han, M. et al., "Saccharification and Ethanol Fermentation from Uncooked Starch Using *Aspergillus niger* Koji," Korean J. Food Sci. Technol., vol. 17, No. 4,pp. 258-264 91985).

Hayashida et al., "High Concentration-Ethanol Fermentation of Raw Ground Corn", Agric. Biol. Chem., 46(7), 1947-1950 (1982).

Hayashida et al., "Molecular cloning of Glucoamylase 1 Gene of *Aspergillus awamori* var. *kawachi* for Localization of the Raw-starch-affinity site", Agric. Biol. Chem., 53(4), 923-929 (1989).

Hayashida et al., Raw Starch-digestive Glucoamulase Productivity of Protease-less Mutant from *Asoergukkys awaniru* var. *kawachi*, Agric. Biol. Chem., 45(12)m p. 2675-2681, 1981.

Honeyman et al., "Evaluation of a Distillers Dried Grain Derivative Feedstuff on Performance of Nursery Pigs", Iowa State University (Internet Mar. 2003).

Islam et al., "Stability of virginiamycin and penicillin during alcohol fermentation", Biomass and Bioenergy, 17: 369-376 (1999).

Iwata et al. "Purification and Characterization of Rice, Alpha.-glucosidase, a key enzyme for Alcohol Fermentation of Rice Polish" Journal of Bioscience and Bioengineering, vol. 95, issue 1, p. 106-108, 2003.

Jacques et al., The Alcohol Textbook, 3rd Edition, A reference for the beverage, fuel and industrial alcohol industries, Nottingham University Press 1999, Alltech Inc. 1999 (386 pages).

Jacques et al., The Alcohol Textbook, 4th Edition, A reference for the beverage, fuel and industrial alcohol industries, Nottingham University Press 2003 Alltech Inc. 203 (446 pages).

Jensen et al., "Purification of extracellular amylolytic enzymes from the thermophilic fungus *Thermomyces lanuginosus*", Can. J. Microbiol., vol. 34, 218-223 (1988).

Jones, "review: Biological principles for the effects of ethanol", Enzyme Microb. Technol., vol. 11, pp. 130-153 (Mar. 1989).

Joutsjoki et al., "A Novel Glucoamylase Preparation for Grain Mash Saccharification", Biotechnology Letters, vol. 15, No. 3, pp. 227-282 (Mar. 1993).

Kang, H. et al., "Effect of Initiation Factor eIF-5A Depletion on Protein Synthesis and Proliferation of *Saccharomyces cerevisiae*," J. Biol. Chem., vol. 269, No. 6, pp. 3934-3940 (Feb. 11, 1994).

Knott et al. "Effects of the Nutrient variability of Distiller's Solubles and Grains within Ethanol Plants and the Amount of Distiller's Solubles Blended with Distiller's Grains on Fat, Protein end Phosphorus Content of DDGS." 2004.

Knott et al. "Variation in Particle Size and Bulk Density of Distiller's Dried Grains with Solubles (DDGS) Produced by 'New Generation' Ethanol Plants in Minnesota and South Dakota." 2004.

Kuyper et al., "Evolutionary engineering of mixed-suger utilization by a xylose-fermenting *Saccharomyces cerevisiae* strain" Fems Yeast Research, vol. 5, 2005, pp. 925-934.

Lang et al., "Recycle Bioreactor for Bioethanol Production from Wheat Starch II. Fermentation and Economics", Energy Sources, 23:427-436 (2001).

Lutzen, "Enzyme Technology in the Production of Ethanol—Recent Process Development", Advances in Biotechnology, vol. II: Fuels, Chemicals, Foods and Waste Treatment, 1981 Pergamon Pres Canada Ltd., pp. 161-167.

Makarov, O. et al. "Quality improvement of table wines following continuous clarification treatments," Kharachova Promislovist (1976)(1 page Abstract).

Matsumoto et al., "Industrialization of a Noncooking System for Alcoholic Fermentation from Grains", Agric. Biol. Chem. 46(6): 1549-1558 (1982).

Matsuoka et al., "Alcoholic Fermentation of Sweet Potato without Cooking", J. Ferment. Technol., vol. 60, No. 6, pp. 599-602 ) (1982).

McAloon et al., "Determining the Cost of Producing Ethanol from Corn Starch and Lignocellulosic Feedstocks", Technical Report NRELTP-580-28893, (Oct. 2000) www.doe.gov/bridge.

McLean et al. A Novel Method for Quantitation of Active Yeast Cells, Technical Report, 3;5-25 (2002).

McLean et al., "Fluorometric Method for Measuring Yeast Metabolic Activity", Technical Report, 3:5-25 (2002).

Mikuni et al., "Alcohol Fermentation of Corn Starch Digested by *Chalara paradoxa* Amylase without Cooking", Biotechnology and Bioengineering, vol. XXIX, p. 729-732 1987.

Minnesota Pollution Control Agency (i.e., MPCA) (2002). Ethanol Production in Minnesota. Air Quality/General #1.20/ Oct. pp. 1-4.

Morris, et al., "AFM Images of Complexes between Amylose and *Aspergillus niger* Glucoamylase Mutants, Native and Mutant Starch Binding Domains: A Model for the Action of glucoamylase", Starch/Starke, 57:1-7 (2005).

Naidu Beesabathuni. "Effect of Corn Flour Particle Size on Ethanol Yield and Soluble Solids in Thin Stillage in a Dry Grind Process." American Society of Agricultural and Biological Engineers, Paper No. 036067, 2003.

Naidu et al., "Effects of Particle Size Reduction on Saccharification in Dry Grind Corn Processing", Department of Agriculture of Biological Engineering, University of Illinois at Urbana Champaign, Poster Presentation 2002 or later.

Narendranath et al., "Acetic Acid Lactic Acid Inhibition of Growth of *Saccharomyces cerevisiae* b Different Mechanisms", American Society of Brewing Chemists, Inc. 59(4): 187-194 (2001).

Narendranath et al., "Effect of yeast inoculation rate on the metabolism of contaminating lactobailli during fermentation of corn mash", J. Ind. Microbiol. Biotechnol, 31:581-584 (2004).

Narendranath et al., "Effects of acetic acid and lactic acid on the growth of *Saccharomyces cerevisiae* in minimal medium", Journal of Industrial Microbiology & Biotechnology, 26: 171-177 (2001).

Narendranath et al., "Effects of *Lactobacilli* on Yeast-Catalyzed Ethanol Fermentations", Applied and Environmental Microbiology, vol. 60, No. 11, p. 4158-4163 (Nov. 1997).

Narendranath et al., "Relationship between pH and Medium Dissolved Solids in Terms of Growth and Metabolism of *Lactobacilli* and *Saccharomyces cerevisiae* during Ethanol Production", Applied and Environmental Microbiology, vol. 71, No. 5, p. 2239-2243 (May 2005).

Narendranath et al., "Urea hydrogen Peroxide Reduces the Number of *Laactobacilli* Nourishes Yeast, and Leaves No Residues in the Ethanol Fermentation", Applied and Environmental Microbiology, vol. 66, No. 10, p. 4187-4192 (Oct. 2000).

Narita et al., "Efficient Production of L-(+)-Lactic Acid from Raw Starch by *Streptococcus bovis* 148" Journal of Bioscience and Bioengineering, vol. 97, No. 6, 423-425 (2004).

Neal St. Anthony, Columnists, "More profit, less waste from ethanol," Star & Tribune, Minneapolis, St. Paul, Minnesota, Date Unknown.

Norman et al., "Process Considerations for the Production of Ethanol from Cereals", Novo Research Institute—Denmark, p. 1-15, Date Unknown.
Patent Title Word Search, Sep. 28, 2005.
PCT Patent Title Word Search, Genencor Assignee, Oct. 4, 2005.
Porter et al., "Variability in Soy Flour Composition", JAOCS, vol. 80, No. 6, pp. 557-562 (2003).
Pourbafrani et al., "Production of biofuels, limonene and pectin from citrus wastes." Bioresource Technology, vol. 101, Feb. 9, 2010. pp. 4246-4250.
Rosentrater, "Understanding Distillers Grain Storage, Handling and Flowability Challenges", Distillers Grain Quarterly, First Quarter 2006, pp. 18-21.
Saha et al., Raw Starch Absorption, Elution and Digestion behavior of Glucoamylase of *Rhizopus niveus*, J. Ferment. Technol., vol. 61, No. 1, p. 67-72, 1983.
Schnier, J. et al., "Translation Initiation Factor 5A and its Hypusine Modification are Essential for Cell Viability in the yeast *Saccharomyces cerevisiae*," Molecular and Cellular Biology, vol. 11, No. 6, pp. 3105-3114 (Jun. 1991).
Shibuya et al., "Molecular Cloning of the Glucoamylase Gene of *Aspergillus shirousami* and its Expression in *Aspergillus oryzae*", Agric. Biol. Chem., 54(8): 1905-1914 (1990).
Shleser, R., "Ethanol Production in Hawaii: Processes, Feedstocks, and Current Economic Feasibility of Fuel Grade Ethanol Produciton in Hawaii" Hawaii State Department of Business, Economic Development & Tourism, Final Report (Jul. 1994).
Shurson, "The Effect of Nutrient Variability of Corn on Estimated Nutrient Variability of DDGS" Univeristy of Minnesota, Date Unknown.
Shurson, J., "Overview of Swine Nutrition Research on the Value and Application of Distiller's Dried Grains with Solubles Produced by Minnesota and South Dakota Ethanol Plants", pp. 1-40 (Internet Mar. 2003).
Shurson, "The Value of High-Protein Distillers Coproducts in Swine Feeds." Distillers Grains Quarterly, First Quarter, pp. 22-25, 2006.
Sigmund et al., "The Economics of Fair Play", Scientific American, pp. 83-87 (Jan. 2002).
Singleton, P. et al., 1991. Dictionary of Microbiology and Molecular Biology, 1991. John Wiley and Sons. p. 964, col. I, II. 45-48.
Springer Link-Article, Web Page—Article—Natural Resources—"Ethanol Fuels: Energy Balance, Economics, and Environmental Impacts are Negative", Printed Jul. 5, 2005, pp. 1-2.
Supplementary European Search Report Dated Sep. 21, 2010 in EP application 04719274.
Suresh, K. et al., "Production of ethanol by raw starch hydrolysis and fermentation of damaged grains of wheat and sorghum," Bioprocess Engineering, vol. 21, pp. 165-168 (1999).
Swanson, Company Spotlight, "Partnering in Progress", Ethanol Producer Magazine, pp. 62-68, Dec. 2004.
Taylor et al., "Dry-Grind Process for Fuel Ethanol by Continuous Fermentation and Stripping", American Chemical Society and American Institute of Chemical Engineers, accepted for publication Mar. 27, 2000, p. A-G.
Taylor et al., "Some Properties of a Glucoamylase produced by the Thermophilic Fungus *Humicola lanuginose*", Carbohydrate Research, 61:301-308 (1978).
Thammarutwasik et al., "Alcoholic Fermentation of Sorghum Without Cooking", Biotechnology and Bioengineering, vol. 28 pp. 1122-1125 (Jul. 1986).
The fuel of the future, Novozymes (May 2002).
Thomas et al., "Fuel Alcohol Production: Effects of Free Amino Nitrogen on Fermentation of Very-High-Gravity Wheat Mashes", Applied and Environmental Microbiology, vol. 56, No. 7, p. 2046-2050 (Jul. 1990).
Tosi et al., "Purification and characterization of an extracellular glucoamylase from the thermophilic fungus *Humicola grisea* var. *thermoidea*", Can J. Microbiol., vol. 36, pp. 846-852 (1993).
Tritto et al., "2 grants, 6 clients boot yields at ethanol center", St. Louis Business Journal, Nov. 26-Dec. 2, 2004.

Ueda et al., "Alcoholic Fermentation of Raw Starch without Cooking by Using Back-koji Amylase", J. Ferment. Technol., vol. 58, No. 3, p. 237-242 (1980).
Ueda et al., "Direct hydrolysis of raw starch", Microbiological Sciences, vol. 1, No. 1, pp. 21-24 (1984).
Ueda, "Ethanol Fermentation of Starch Materials without Cooking", J. Jap. Soc. Starch Sci., 29(2):123-130 (1982), (English Abstract).
Van Maris et al., "Alcoholic fermentation of carbon sources in biomass hydrolysates by *Saccharomyces cerevisiae*: current status," Antionie Van Leeuwenhoek, vol. 90, 2006, pp. 391-418.
Van Uden et al., "Effects of ethanol on yeast performance; targets and underlying mechanisms", European Brewery Convention, Proceeding of the 19.sup.th Congress, London (1983) pp. 137-144.
Viitanen et al., "Production of a xylose utilizing *Zymomonas mobilis* strain for ethanol production from high concentrations of mixed sugars" 31st symposium on biotechnology for fuels and chemicals; San Francisco, CA May 2009, pp. 48-48.
Wang, "Argonne National Laboratory Ethanol Study: Key points." Office of Energy Efficiency and Renewal Energy—U.S. Department of Energy, pp. 1-3, 2005.
Waxy Corn, U.S. Grains Council, pp. 1-8 (Internet Mar. 2003).
Weigel et al., "Feed Co-Products of the Dry Corn Milling Process", Feed Co-Products Handbook, pp. 1-13 (Internet Mar. 2003).
Weiss et al. Updated 2009 Distillers Grains—eXtension, pp. 1-6, Printed 05:08/1010.
Weller et al., "Fuel Ethanol from Raw Corn by *Aspergilli* Hydrolysis with Concurrent Yeast Fermentation", Biotechnology and Bioengineering Symp., No. 13, pp. 437-447 (1983).
www.nrel.gov/docs/fy02osti/31195.pdf. Biofuels News. vol. 4. No. 3. Fall 2001.
Yue et al., Functionality of resistant starch in food applications:, National Starch & Chemical (reprinted from Dec. 1998 issue of Food Australia) (1999).
Zheng et al., "Enzymatic saccharification of the dilute acid pretreated saline crops for fermentable sugar production." Applied Energy, vol. 86, Apr. 11, 2009. pp. 2459-2465.
Ziffer et al., 1982. "Temperature Effects in Ethanol Fermentation High Corn Media." Biotechnology Letters. vol. 4, No. 12, pp. 809-814.
Extended European Search Report dated Oct. 29 2012 in related European Application Serial No. 12184429.4.
de Mancilha, et al, Evaluation of Ion Exchange Resins for Removal of Inhibitory Compounds from Corn Stover Hydrolyzate for Xylitol Fermentation, Biotechnology Progress, 19:1837-1841 (2003).
Jeffries, T.W., et al., Fermentation of Hemicellulosic Sugars and Sugar Mixtures by *Candida shehatae*, Biotechnology and Bioengineering, 31:502-506 (1988).
Nilvebrandt, et al., Detoxification of Lignocellulose Hydrolysates with Ion-Exchange Resins, Applied Biochemistry and Biotechnology, 91-93:35-49 (2001).
Taherzadeh, et al., Pretreatment of Lignocellulosic Wastes to Improve Ethanol and Biogas Production: A Review, Int. J. Mol. Sci., 9:1621-1651 (2008).
US Office Action dated Apr. 20, 2012 in related U.S. Appl. No. 12/716,989.
US Office Action dated May 7, 2012 in related U.S. Appl. No. 12/717,002.
US Office Action dated Jun. 20, 2012 in related U.S. Appl. No. 12/581,076.
US Office Action dated Sep. 4, 2012 in related U.S. Appl. No. 12/717,015.
US Office Action dated Aug. 1, 2012 in related U.S. Appl. No. 12/716,984.

* cited by examiner

METHODS AND SYSTEMS FOR PRODUCING ETHANOL USING RAW STARCH AND FRACTIONATION

CROSS-REFERENCE TO RELATED APPLICATIONS

This Application is a Continuation Patent Application of U.S. patent application Ser. No. 11/682,195, filed Mar. 5, 2007, which is a Continuation of U.S. patent application Ser. No. 11/077,969, filed Mar. 10, 2005, now abandoned, which claims the benefit under 35 U.S.C. §119(e) of U.S. Provisional Application Ser. Nos. 60/614,916, filed Sep. 30, 2004, 60/615,155, filed Oct. 1, 2004, and 60/552,108, filed Mar. 10, 2004 and which is a Continuation-In-Part of U.S. patent application Ser. No. 10/798,226, filed Mar. 10, 2004 now abandoned, which claims priority to 60/453,442, filed Mar. 10, 2003, each of which are hereby incorporated by reference in their entirety.

FIELD OF THE INVENTION

The present invention relates to methods for producing high levels of alcohol during fermentation of plant material, and to the high alcohol beer produced. The method can include fractionating the plant material. The present invention also relates to methods for producing high protein distiller's dried grain from fermentation of plant material, and to the high protein distiller's dried grain produced. The method can include drying a co-product by ring drying, flash drying, or fluid bed drying. The present invention further relates to reduced stack emissions from drying distillation products from the production of ethanol.

BACKGROUND OF THE INVENTION

Numerous conventional methods exist for converting plant material to ethanol. However, these methods suffer from numerous inefficiencies. There remains a need for additional more effective methods for converting plant material to ethanol and for producing improved fermentation products.

SUMMARY OF THE INVENTION

The present invention relates to methods for producing high levels of alcohol during fermentation of plant material, and to the high alcohol beer produced. The method can include fractionating the plant material. The present invention also relates to methods for producing high protein distiller's dried grain from fermentation of plant material, and to the high protein distiller's dried grain produced. The method can include drying a co-product by ring drying, flash drying, or fluid bed drying.

In an embodiment, the present invention relates to a process for producing ethanol from plant material (e.g., fractionated plant material). This method includes fractionating the plant material; grinding the plant material (e.g., fractionated plant material) to produce ground plant material (e.g., fractionated plant material) including starch; saccharifying the starch, without cooking; fermenting the incubated starch; and recovering the ethanol from the fermentation. The present method can include varying the temperature during fermentation. The present method can include employing plant material (e.g., fractionated plant material) with a particle size such that more than 50% of the material fits though a sieve with a 0.5 mm mesh. The present method can yield a composition including at least 18 vol-% ethanol.

In an embodiment, the present invention relates to a process for producing high protein distiller's dried grain from plant material (e.g., fractionated plant material). This method includes fractionating the plant material; grinding the plant material (e.g., fractionated plant material) to produce ground plant material (e.g., fractionated plant material) including starch; producing sugars from the starch without cooking; fermenting the uncooked sugars to yield a composition including ethanol; and recovering distiller's dried grain from the fermentation. The distiller's dried grain can include at least about 30% protein. The distillers dried grain can include increased levels of the protein zein.

In an embodiment, the present invention relates to a process of producing ethanol from corn. This process includes producing starch from corn and ethanol from the starch; producing dryer stack emissions including a significantly lower level of volatile organic compounds than conventional technologies.

DETAILED DESCRIPTION OF THE INVENTION

Definitions

Figure 1:
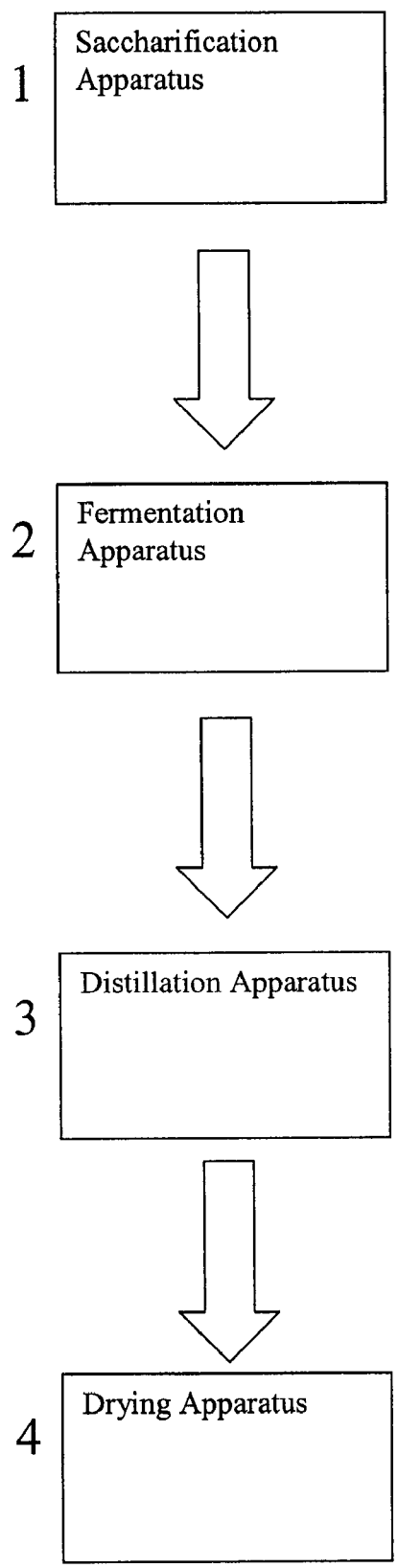
FIG. 1 schematically illustrates a fermentation system according to an embodiment of the present invention.

As used herein, the phrase "without cooking" refers to a process for converting starch to ethanol without heat treatment for gelatinization and dextrinization of starch using alpha-amylase. Generally, for the process of the present invention, "without cooking" refers to maintaining a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polymer type. In the method of the present invention, dextrinization of starch using conventional liquefaction techniques is not necessary for efficient fermentation of the carbohydrate in the grain.

As used herein, the phrase "plant material" refers to all or part of any plant (e.g., cereal grain), typically a material including starch. Suitable plant material includes grains such as maize (corn, e.g., whole ground corn), sorghum (milo), barley, wheat, rye, rice, and millet; and starchy root crops, tubers, or roots such as sweet potato and cassava. The plant material can be a mixture of such materials and byproducts of such materials, e.g., corn fiber, corn cobs, stover, or other cellulose and hemicellulose containing materials such as wood or plant residues. Suitable plant materials include corn, either standard corn or waxy corn.

As used herein, the phrase "fractionated plant material" refers to plant material that includes only a portion or fraction of the total plant material, typically a material including starch. Fractionated plant material can include fractionated grains such as fractionated maize (fractionated corn), fractionated sorghum (fractionated milo), fractionated barley, fractionated wheat, fractionated rye, fractionated rice, and fractionated millet; and fractionated starchy root crops, tubers, or roots such as fractionated sweet potato and fractionated cassava. Suitable fractionated plant materials include fractionated corn, either fractionated standard corn or fractionated waxy corn.

As used herein, the terms "saccharification" and "saccharifying" refer to the process of converting starch to smaller polysaccharides and eventually to monosaccharides, such as glucose. Conventional saccharification uses liquefaction of gelatinized starch to create soluble dextrinized substrate which glucoamylase enzyme hydrolyzes to glucose. In the present method, saccharification refers to converting raw starch to glucose with enzymes, e.g., glucoamylase and acid fungal amylase (AFAU). According to the present method, the raw starch is not subjected to conventional liquefaction and gelatinization to create a conventional dextrinized substrate.

As used herein, a unit of acid fungal amylase activity (AFAU) refers to the standard Novozymes units for measuring acid fungal amylase activity. The Novozymes units are described in a Novozymes technical bulletin SOP No.: EB-SM-0259.02/01. Such units can be measured by detecting products of starch degradation by iodine titration. 1 unit is defined as the amount of enzyme that degrades 5.260 mg starch dry matter per hour under standard conditions.

As used herein, a unit of glucoamylase activity (GAU) refers to the standard Novozymes units for measuring glucoamylase activity. The Novozymes units and assays for determining glucoamylase activity are described in a publicly available Novozymes technical bulletin.

As used herein, a unit of amyloglucosidase activity (AGU) refers to the standard Novozymes units for measuring amyloglucosidase activity. The Novozymes units are described in a Novozymes technical bulletin SOP No.: EB-SM-0131.02/01. Such units can be measured by detecting conversion of maltose to glucose. The glucose can be determined using the glucose dehydrogenase reaction. 1 unit is defined as the amount of enzyme that catalyzes the conversion of 1 mmol maltose per minute under the given conditions.

As used herein, the term "about" modifying any amount refers to the variation in that amount encountered in real world conditions of producing sugars and ethanol, e.g., in the lab, pilot plant, or production facility. For example, an amount of an ingredient employed in a mixture when modified by "about" includes the variation and degree of care typically employed in measuring in an ethanol production plant or lab. For example, the amount of a component of a product when modified by "about" includes the variation between batches in an ethanol production plant or lab and the variation inherent in the analytical method. Whether or not modified by "about," the amounts include equivalents to those amounts. Any quantity stated herein and modified by "about" can also be employed in the present invention as the amount not modified by "about."

Converting Starch to Ethanol

The present invention relates to methods for producing high levels of alcohol during fermentation of plant material (e.g., fractionated plant material), and to the high alcohol beer produced. The present invention also relates to methods for producing high protein distiller's dried grain from fermentation of plant material (e.g., fractionated plant material), to the high protein distiller's dried grain produced, and to the cleaner dryer stack emissions.

The present method converts starch from plant material (e.g., fractionated plant material) to ethanol. In an embodiment, the present method can include preparing the plant material (e.g., fractionated plant material) for saccharification, converting the prepared plant material (e.g., fractionated plant material) to sugars without cooking, and fermenting the sugars.

The plant material (e.g., fractionated plant material) can be prepared for saccharification by any a variety of methods, e.g., by grinding, to make the starch available for saccharification and fermentation. In an embodiment, the vegetable material can be ground so that a substantial portion, e.g., a majority, of the ground material fits through a sieve with a 0.1-0.5 mm screen. For example, in an embodiment, about 70% or more, of the ground vegetable material can fit through a sieve with a 0.1-0.5 mm screen. In an embodiment, the reduced plant material (e.g., fractionated plant material) can be mixed with liquid at about 20 to about 50 wt-% or about 25 to about 45 wt-% dry reduced plant material (e.g., fractionated plant material).

The present process can include converting reduced plant material (e.g., fractionated plant material) to sugars that can be fermented by a microorganism such as yeast. This conversion can be effected by saccharifying the reduced plant material (e.g., fractionated plant material) with an enzyme preparation, such as a saccharifying enzyme composition. A saccharifying enzyme composition can include any of a variety of known enzymes suitable for converting reduced plant material (e.g., fractionated plant material) to fermentable sugars, such as amylases (e.g., α-amylase and/or glucoamylase). In an embodiment, saccharification is conducted at a pH of about 6.0 or less, for example, about 4.5 to about 5.0, for example, about 4.5 to about 4.8.

The present process includes fermenting sugars from reduced plant material (e.g., fractionated plant material) to ethanol. Fermenting can be effected by a microorganism, such as yeast. In an embodiment, fermentation is conducted at a pH of about 6 or less, for example, about 4.5 to about 5, for example, about 4.5 to about 4.8. In an embodiment, the present method can include varying the pH. For example, fermentation can include filling the fermenter at pH of about 3 to about 4.5 during the first half of fill and at a pH of about 4.5 to about 6 (e.g., about 4.5 to about 4.8) during the second half of the fermenter fill cycle. In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, fermentation is conducted for about 25 (e.g., 24) to about to 150 hours, for example, for about 48 (e.g., 47) to about 96 hours.

The present process can include simultaneously converting reduced plant material (e.g., fractionated plant material) to sugars and fermenting those sugars with a microorganism such as yeast.

The product of the fermentation process is referred to herein as "beer". Ethanol can be recovered from the fermentation mixture, from the beer, by any of a variety of known processes, such as by distilling. The remaining stillage includes both liquid and solid material. The liquid and solid can be separated by, for example, centrifugation.

Preparing the Plant Material

The present method converts starch from plant material (e.g., fractionated plant material) to ethanol. The plant material (e.g., fractionated plant material) can be reduced by a variety of methods, e.g., by grinding, to make the starch available for saccharification and fermentation. Other methods of plant material reduction are available. For example, vegetable material, such as kernels of corn, can be ground with a ball mill, a roller mill, a hammer mill, or another mill known for grinding vegetable material, and/or other materials for the purposes of particle size reduction. The use of emulsion technology, rotary pulsation, and other means of particle size reduction can be employed to increase surface area of plant material (e.g., fractionated plant material) while raising the effectiveness of flowing the liquefied media. The prepared plant material (e.g., fractionated plant material) can be referred to as being or including "raw starch".

A fine grind exposes more surface area of the plant material (e.g., fractionated plant material), or vegetable material, and can facilitate saccharification and fermentation. In an embodiment, the vegetable material is ground so that a substantial portion, e.g., a majority, of the ground material fits through a sieve with a 0.1-0.5 mm screen. In an embodiment, about 35% or more of the ground vegetable material can fit through a sieve with a 0.1-0.5 mm screen. In an embodiment, about 35 to about 70% of the ground vegetable material can fit through a sieve with a 0.1-0.5 mm screen. In an embodiment, about 50% or more of the ground vegetable material can fit through a sieve with a 0.1-0.5 mm screen. In an embodiment, about 90% of the ground vegetable material can fit through a sieve with a 0.1-0.5 mm screen. In an embodiment, all of the ground vegetable material can fit through a sieve with a 0.1-0.5 mm screen. In an embodiment, the ground vegetable material has an average particle size of about 0.25 mm.

Plant Material Reduction

Preparing the plant material (e.g., fractionated plant material) can employ any of a variety of techniques for plant material (e.g., fractionated plant material) reduction. For example, the present method of preparing plant material (e.g., fractionated plant material) can employ emulsion technology, rotary pulsation, sonication, magnetostriction, ferromagnetic materials, or the like. These methods of plant material reduction can be employed for substrate pretreatment. Although not limiting to the present invention, it is believed that these methods can increase surface area of plant material (e.g., fractionated plant material) while raising the effectiveness of flowing of liquefied media (i.e. decreased viscosity). These methods can include electrical to mechanical, mechanical to electrical, pulse, and sound based vibrations at varying speeds. This can provide varying frequencies over a wide range of frequencies, which can be effective for pretreating the plant material (e.g., fractionated plant material) and/or reducing particle size.

Although not limiting to the present invention, it is believed that certain of these sonic methods create low pressure around a particle of plant material (e.g., fractionated plant material) and induce cavitation of the particle or disruption of the particle structure. The cavitated or disrupted particle can increase availability of plant material (e.g., starch) to an enzyme, for example, by increasing surface area. It is believed that such pretreatment can decrease quantity of enzyme rates in the present method for ethanol production.

In an embodiment, the present method includes vibrating plant material (e.g., fractionated plant material) and cavitating the fluid containing the plant material. This can result in disrupting the plant material and/or decreasing the size of the plant material (e.g., fractionated plant material). In certain embodiments, the present method includes treating plant material (e.g., fractionated plant material) with emulsion technology, with rotary pulsation, with magnetostriction, or with ferromagnetic materials. This can result in disrupting the plant material and/or decreasing the size of the plant material (e.g., fractionated plant material). In an embodiment, the present method includes sonicating the plant material (e.g., fractionated plant material). This can result in disrupting the plant material and/or decreasing the size of the plant material (e.g., fractionated plant material).

In an embodiment, the present method can include employing sound waves for reducing plant material (e.g., fractionated plant material). The sound waves can be ultrasound. The present method can include sonicating the plant material (e.g., fractionated plant material). The method can include sonicating the plant material at a frequency (e.g., measured in kHz), power (e.g., measured in watts), and for a time effective to reduce (or to assist in reducing) the particle size to sizes described hereinabove. For example, the method can include sonicating the plant material (e.g., fractionated plant material) at 20,000 Hz and up to about 3000 W for a sufficient time and at a suitable temperature. Such sonicating can be carried out with commercially available apparatus, such as high powered ultrasonics available from ETREMA (Ames, Iowa).

In an embodiment, the present method can include employing rotary pulsation for reducing plant material (e.g., fractionated plant material). The method can include rotary pulsating the plant material (e.g., fractionated plant material) at a frequency (e.g., measured in Hz), power (e.g., measured in watts), and for a time effective to reduce (or to assist in reducing) the particle size to sizes described hereinabove. Such rotary pulsating can be carried out with known apparatus, such as apparatus described in U.S. Pat. No. 6,648,500, the disclosure of which is incorporated herein by reference.

In an embodiment, the present method can include employing pulse wave technology for reducing plant material (e.g., fractionated plant material). The method can include rotary pulsing the plant material at a frequency (e.g., measured in Hz), power (e.g., measured in watts), and for a time effective to reduce (or to assist in reducing) the particle size to sizes described hereinabove. Such pulsing can be carried out with known apparatus, such as apparatus described in U.S. Pat. No. 6,726,133, the disclosure of which is incorporated herein by reference.

Fractionation

In an embodiment, the vegetable material can be fractionated into one or more components. For example, a vegetable material such as a cereal grain or corn can be fractionated into components such as fiber (e.g., corn fiber), germ (e.g., corn germ), and a mixture of starch and protein (e.g., a mixture of corn starch and corn protein). One or a mixture of these components can be fermented in a process according to the present invention. Fractionation of corn or another plant material can be accomplished by any of a variety of methods or apparatus. For example, a system manufactured by Satake can be used to fractionate plant material such as corn.

In an embodiment, the germ and fiber components of the vegetable material can be fractionated and separated from the remaining portion of the vegetable material. In an embodiment, the remaining portion of the vegetable material (e.g., corn endosperm) can be further milled and reduced in particle size and then combined with the larger pieces of the fractioned germ and fiber components for fermenting.

In an embodiment, the vegetable material can be milled to access value added products (such as neutraceuticals, leutein, carotenoids, xanthrophils, pectin, cellulose, lignin, mannose, xylose, arabinose, galactose, galacturonic acid, GABA, corn oil, albumins, globulins, prolamins, gluetelins, zein and the like).

Fractionation can be accomplished by any of a variety of methods and apparatus, such as those disclosed in U.S. Patent Application Publication No. 2004/0043117, the disclosure of which is incorporated herein by reference. Suitable methods and apparatus for fractionation include a sieve, sieving, and elutriation. Suitable apparatus include a frictional mill such as a rice or grain polishing mill (e.g., those manufactured by Satake, Kett, or Rapsco)

Saccharification and Fermentation

Saccharification

The present process can include converting reduced plant material (e.g., fractionated plant material) to sugars that can be fermented by a microorganism such as yeast. This conversion can be effected by saccharifying the reduced plant material (e.g., fractionated plant material) with any of a variety of known saccharifying enzyme compositions. In an embodiment, the saccharifying enzyme composition includes an amylase, such as an alpha amylase (e.g., an acid fungal amylase). The enzyme preparation can also include glucoamylase. The enzyme preparation need not, and, in an embodiment, does not include protease. However, ethanol production methods according to the present invention can conserve water by reusing process waters (backset) which may contain protease. In an embodiment, the present method employs acid fungal amylase for hydrolyzing raw starch.

Saccharifying can be conducted without cooking. For example, saccharifying can be conducted by mixing source of saccharifying enzyme composition (e.g., commercial enzyme), yeast, and fermentation ingredients with ground grain and process waters without cooking.

In an embodiment, saccharifying can include mixing the reduced plant material (e.g., fractionated plant material) with a liquid, which can form a slurry or suspension and adding saccharifying enzyme composition to the liquid. In an embodiment, the method includes mixing the reduced plant material (e.g., fractionated plant material) and liquid and then adding the saccharifying enzyme composition. Alternatively, adding enzyme composition can precede or occur simultaneously with mixing.

In an embodiment, the reduced plant material (e.g., fractionated plant material) can be mixed with liquid at about 20 to about 50 wt-%, about 25 to about 45 (e.g., 44) wt-%, about 30 to about 40 (e.g., 39) wt-%, or about 35 wt-% dry reduced plant material (e.g., fractionated plant material). As used herein, wt-% of reduced plant material in a liquid refers to the percentage of dry substance reduced plant material or dry solids. In an embodiment, the method of the present invention can convert raw or native starch (e.g., in dry reduced plant material) to ethanol at a faster rate at higher dry solids levels compared to conventional saccharification with cooking. Although not limiting to the present invention, it is believed that the present method can be practiced at higher dry solids levels because, unlike the conventional process, it does not include gelatinization, which increases viscosity.

Suitable liquids include water and a mixture of water and process waters, such as stillage (backset), scrubber water, evaporator condensate or distillate, side stripper water from distillation, or other ethanol plant process waters. In an embodiment, the liquid includes water. In an embodiment, the liquid includes water in a mixture with about 1 to about 70 vol-% stillage, about 15 to about 60 vol-% stillage, about 30 to about 50 vol-% stillage, or about 40 vol-% stillage.

In the conventional process employing gelatinization and liquefaction, stillage provides nutrients for efficient yeast fermentation, especially free amino nitrogen (FAN) required by yeast. The present invention can provide effective fermentation with reduced levels of stillage and even without added stillage. In an embodiment, the present method employs a preparation of plant material (e.g., fractionated plant material) that supplies sufficient quantity and quality of nitrogen for efficient fermentation under high gravity conditions (e.g., in the presence of high levels of reduced plant material). Thus, in an embodiment, no or only low levels of stillage can suffice.

However, the present method provides the flexibility to employ high levels of stillage if desired. The present method does not employ conventional liquefaction. Conventional liquefaction increases viscosity of the fermentation mixture and the resulting stillage. The present method produces lower viscosity stillage. Therefore, in an embodiment, increased levels of stillage can be employed in the present method without detrimental increases in viscosity of the fermentation mixture or resulting stillage.

Further, although not limiting to the present invention, it is believed that conventional saccharification and fermentation processes require added FAN due to undesirable "Maillard Reactions" which occur during high temperature gelatinization and liquefaction. The Maillard Reactions consume FAN during cooking. As a result, the conventional process requires adding stillage (or another source of FAN) to increase levels of FAN in fermentation. It is believed that the present process avoids temperature induced Maillard Reactions and provides increased levels of FAN in the reduced plant material, which are effectively utilized by the yeast in fermentation.

Saccharification can employ any of a variety of known enzyme sources (e.g., a microorganism) or compositions to produce fermentable sugars from the reduced plant material (e.g., fractionated plant material). In an embodiment, the saccharifying enzyme composition includes an amylase, such as an alpha amylase (e.g., an acid fungal amylase) or a glucoamylase.

In an embodiment, saccharification is conducted at a pH of about 6.0 or less, pH of about 3.0 to about 6.0, about 3.5 to about 6.0, about 4.0 to about 5.0, about 4.0 to about 4.5, about 4.5 to about 5.0, or about 4.5 to about 4.8. In an embodiment, saccharification is conducted at a pH of about 4.1 to about 4.6 or about 4.9 to about 5.3. The initial pH of the saccharification mixture can be adjusted by addition of, for example, ammonia, sulfuric acid, phosphoric acid, process waters (e.g., stillage (backset), evaporator condensate (distillate), side stripper bottoms, and the like), and the like. Activity of certain saccharifying enzyme compositions (e.g., one including acid fungal amylase) can be enhanced at pH lower than the above ranges.

In an embodiment, saccharification is conducted at a temperature of about 25 to about 40° C. or about 30 to about 35° C.

In an embodiment, saccharifying can be carried out employing quantities of saccharifying enzyme composition selected to maintain low concentrations of dextrin in the fermentation broth. For example, the present process can employ quantities of saccharifying enzyme composition selected to maintain maltotriose (DP3) at levels at or below about 0.2 wt-% or at or below about 0.1 wt-%. For example, the present process can employ quantities of saccharifying enzyme composition selected to maintain dextrin with a degree of polymerization of 4 or more (DP4+) at levels at or below about 1 wt-% or at or below about 0.5 wt-%.

In an embodiment, saccharifying can be carried out employing quantities of saccharifying enzyme composition selected to maintain low concentrations of maltose in the fermentation broth. For example, the present process can employ quantities of saccharifying enzyme composition selected to maintain maltose at levels at or below about 0.3 wt-%. For maintaining low levels of maltose, suitable levels of acid fungal amylase and glucoamylase include about 0.05 to about 3 AFAU/gram dry solids reduced plant material (e.g., DSC) of acid fungal amylase and about 1 to about 2.5 (e.g., 2.4) AGU per gram dry solids reduced plant material (e.g., DSC) of glucoamylase. In an embodiment, the reaction mixture includes about 0.1 to about 2 AFAU/gram dry solids reduced plant material (e.g., DSC) of acid fungal amylase and about 1 to about 2.5 AGU per gram dry solids reduced plant material (e.g., DSC) of glucoamylase. In an embodiment, the reaction mixture includes about 0.3 to about 2 AFAU/gram dry solids reduced plant material (e.g., DSC) of acid fungal amylase and about 1 to about 2.5 AGU per gram dry solids reduced plant material (e.g., DSC) of glucoamylase. In an embodiment, the reaction mixture includes about 1 to about 2 AFAU/gram dry solids reduced plant material (e.g., DSC) of acid fungal amylase and about 1 to about 1.5 AGU per gram dry solids reduced plant material (e.g., DSC) of glucoamylase.

Glucoamylase

In certain embodiments, the present method can employ a glucoamylase. Glucoamylase is also known as amyloglucosidase and has the systematic name 1,4-alpha-D-glucan glucohydrolase (E.C. 3.2.1.3). Glucoamylase refers to an enzyme that removes successive glucose units from the non-reducing ends of starch. For example, certain glucoamylases can hydrolyze both the linear and branched glucosidic linkages of starch, amylose, and amylopectin. A variety of suitable glucoamylases are known and commercially available. For example, suppliers such as Novozymes and Genencor provide glucoamylases. The glucoamylase can be of fungal origin.

The amount of glucoamylase employed in the present process can vary according to the enzymatic activity of the amylase preparation. Suitable amounts include about 0.05 to about 6.0 glucoamylase units (AGU) per gram dry solids reduced plant material (e.g., DSC). In an embodiment, the reaction mixture can include about 1 to about 6 AGU per gram dry solids reduced plant material (e.g., DSC). In an embodiment, the reaction mixture can include about 1 to about 3 AGU per gram dry solids reduced plant material (e.g., DSC). In an embodiment, the reaction mixture can include about 1 to about 2.5 (e.g., 2.4) AGU per gram dry solids reduced plant material (e.g., DSC). In an embodiment, the reaction mixture can include about 1 to about 2 AGU per gram dry solids reduced plant material (e.g., DSC). In an embodiment, the reaction mixture can include about 1 to about 1.5 AGU per gram dry solids reduced plant material (e.g., DSC). In an embodiment, the reaction mixture can include about 1.2 to about 1.5 AGU per gram dry solids reduced plant material (e.g., DSC).

Acid Fungal Amylase

In certain embodiments, the present method employs an α-amylase. The α-amylase can be one produced by fungi. The α-amylase can be one characterized by its ability to hydrolyze carbohydrates under acidic conditions. An amylase produced by fungi and able to hydrolyze carbohydrates under acidic conditions is referred to herein as acid fungal amylase, and is also known as an acid stable fungal α-amylase. Acid fungal amylase can catalyze the hydrolysis of partially hydrolyzed starch and large oligosaccharides to sugars such as glucose. The acid fungal amylase that can be employed in the present process can be characterized by its ability to aid the hydrolysis of raw or native starch, enhancing the saccharification provided by glucoamylase. In an embodiment, the acid fungal amylase produces more maltose than conventional (e.g., bacterial) α-amylases.

Suitable acid fungal amylase can be isolated from any of a variety of fungal species, including *Aspergillus, Rhizopus, Mucor, Candida, Coriolus, Endothia, Enthomophtora, Irpex, Penicillium, Sclerotium* and *Torulopsis* species. In an embodiment, the acid fungal amylase is thermally stable and is isolated from *Aspergillus* species, such as *A. niger, A. saitoi* or *A. oryzae*, from *Mucor* species such as *M. pusillus* or *M. miehei*, or from *Endothia* species such as *E. parasitica*. In an embodiment, the acid fungal amylase is isolated from *Aspergillus niger*. The acid fungal amylase activity can be supplied as an activity in a glucoamylase preparation, or it can be added as a separate enzyme. A suitable acid fungal amylase can be obtained from Novozymes, for example in combination with glucoamylase.

The amount of acid fungal amylase employed in the present process can vary according to the enzymatic activity of the amylase preparation. Suitable amounts include about 0.1 to about 10 acid fungal amylase units (AFAU) per gram of dry solids reduced plant material (e.g., dry solids corn (DSC)). In an embodiment, the reaction mixture can include about 0.05 to about 3 AFAU/gram dry solids reduced plant material (e.g., DSC). In an embodiment, the reaction mixture can include about 0.1 to about 3 AFAU/gram dry solids reduced plant material (e.g., DSC). In an embodiment, the reaction mixture can include about 0.3 to about 3 AFAU/gram dry solids reduced plant material (e.g., DSC). In an embodiment, the reaction mixture can include about 1 to about 2 AFAU/gram dry solids reduced plant material (e.g., DSC).

Fermenting

The present process includes fermenting sugars from reduced plant material (e.g., fractionated plant material) to ethanol. Fermenting can be effected by a microorganism, such as yeast. The fermentation mixture need not, and in an embodiment does not, include protease. However, the process waters may contain protease. The amount of protease can be less than that used in the conventional process. According to the present invention, fermenting is conducted on a starch composition that has not been cooked. In an embodiment, the present fermentation process produces potable alcohol. Potable alcohol has only acceptable, nontoxic levels of other alcohols, such as fusel oils. Fermenting can include contacting a mixture including sugars from the reduced plant material (e.g., fractionated plant material) with yeast under conditions suitable for growth of the yeast and production of ethanol. In an embodiment, fermenting employs the saccharification mixture.

Any of a variety of yeasts can be employed as the yeast starter in the present process. Suitable yeasts include any of a variety of commercially available yeasts, such as commercial strains of *Saccharomyces cerevisiae*. Suitable strains include "Fali" (Fleischmann's), Thermosac (Alltech), Ethanol Red (LeSafre), BioFerm AFT (North American Bioproducts), and the like. In an embodiment, the yeast is selected to provide rapid growth and fermentation rates in the presence of high temperature and high ethanol levels. In an embodiment, Fali yeast has been found to provide good performance as measured by final alcohol content of greater than 17% by volume.

The amount of yeast starter employed is selected to effectively produce a commercially significant quantity of ethanol in a suitable time, e.g., less than 75 hours.

Yeast can be added to the fermentation by any of a variety of methods known for adding yeast to fermentation processes. For example, yeast starter can be added as a dry batch, or by conditioning/propagating. In an embodiment, yeast starter is added as a single inoculation. In an embodiment, yeast is added to the fermentation during the fermenter fill at a rate of 5 to 100 pounds of active dry yeast (ADY) per 100,000 gallons of fermentation mash. In an embodiment, the yeast can be acclimated or conditioned by incubating about 5 to 50 pounds of ADY per 10,000 gallon volume of fermenter volume in a prefermenter or propagation tank. Incubation can be from 8 to 16 hours during the propagation stage, which is also aerated to encourage yeast growth. The prefermenter used to inoculate the main fermenter can be from 1 to 10% by volume capacity of the main fermenter, for example, from 2.5 to 5% by volume capacity relative to the main fermenter.

In an embodiment, the fermentation is conducted at a pH of about 6 or less, pH of about 3 to about 6, about 3 to about 4.5, about 3.5 to about 6, about 4 to about 5, about 4 to about 4.5, about 4.5 to about 5, or about 4.5 to about 4.8. The initial pH of the fermentation mixture can be adjusted by addition of, for example, ammonia, sulfuric acid, phosphoric acid, process waters (e.g., stillage (backset), evaporator condensate (distillate), side stripper bottoms, and the like), and the like.

Although not limiting to the present invention, it is believed that known distillery yeast grow well over the pH range of 3 to 6, but are more tolerant of lower pH's down to 3.0 than most contaminant bacterial strains. Contaminating lactic and acetic acid bacteria grow best at pH of 5.0 and above. Thus, in the pH range of 3.0 to 4.5, it is believed that ethanol fermentation will predominate because yeast will grow better than contaminating bacteria.

In an embodiment, the present method can include varying the pH. It is believed that varying the pH can be conducted to reduce the likelihood of contamination early in fermentation and/or to increase yeast growth and fermentation during the latter stages of fermentation. For example, fermentation can include filling the fermenter at pH of about 3 to about 4.5 during the first half of fill. Fermentation can include increasing the slurry pH to pH of about 4.5 to about 6 during the second half of the fermenter fill cycle. Fermentation can include maintaining pH by adding fresh substrate slurry at the desired pH as described above. In an embodiment, during fermentation (after filling), pH is not adjusted. Rather, in this embodiment, the pH is determined by the pH of the components during filling.

In an embodiment, the pH is decreased to about five (5) or below in the corn process waters. In an embodiment, the pH is about pH 4 (e.g. 4.1) at the start of fermentation fill and is increased to about pH 5 (e.g. 5.2) toward the end of fermentation fill. In an embodiment, the method includes stopping pH control of the mash slurry after the yeast culture becomes established during the initial process of filling the fermenter, and then allowing the pH to drift up in the corn process waters during the end stages of filling the fermenter.

In an embodiment, fermentation is conducted for about to 25 (e.g., 24) to about to 150 hours, about 25 (e.g., 24) to about 96 hours, about 40 to about 96 hours, about 45 (e.g., 44) to about 96 hours, about 48 (e.g., 47) to about 96 hours. For example, fermentation can be conducted for about 30, about 40, about 50, about 60, or about 70 hours. For example, fermentation can be conducted for about 35, about 45, about 55, about 65, or about 75 hours.

In an embodiment, fermentation is conducted at a temperature of about 25 to about 40° C. or about 30 to about 35° C. In an embodiment, during fermentation the temperature is decreased from about 40° C. to about 30° C. or about 25° C., or from about 35° C. to about 30° C., during the first half of the fermentation, and the temperature is held at the lower temperature for the second half of the fermentation. In an embodiment, the temperature can be decreased as ethanol is produced. For example, in an embodiment, during fermentation the temperature can be as high as about 99° F. and then reduced to about 79° F. This temperature reduction can be coordinated with increased ethanol titers (%) in the fermenter.

In an embodiment, the present method includes solids staging. Solids staging includes filling at a disproportionately higher level of solids during the initial phase of the fermenter fill cycle to increase initial fermentation rates. The solids concentration of the mash entering the fermenter can then be decreased as ethanol titers increase and/or as the fermenter fill cycle nears completion. In an embodiment, the solids concentration can be about 40% (e.g. 41%) during the first half of the fermentation fill. This can be decreased to about 25% after the fermenter is 50% full and continuing until the fermenter fill cycle is concluded. In the above example, such a strategy results in a full fermenter with solids at 33%.

It is believed that solids staging can accelerate enzyme hydrolysis rates and encourage a rapid onset to fermentation by using higher initial fill solids. It is believed that lowering solids in the last half of fill can reduce osmotic pressure related stress effects on the yeast. By maintaining overall fermenter fill solids within a specified range of fermentability, solids staging improves the capacity of the yeast to ferment high gravity mashes toward the end of fermentation.

Simultaneous Saccharification and Fermentation

The present process can include simultaneously converting reduced plant material (e.g., fractionated plant material) to sugars and fermenting those sugars with a microorganism such as yeast. Simultaneous saccharifying and fermenting can be conducted using the reagents and conditions described above for saccharifying and fermenting.

In an embodiment, saccharification and fermentation is conducted at a temperature of about 25 to about 40° C. or about 30 to about 35° C. In an embodiment, during saccharification and fermentation the temperature is decreased from about 40 to about 25° C. or from about 35 to about 30° C. during the first half of the saccharification, and the temperature is held at the lower temperature for the second half of the saccharification.

Although not limiting to the present invention, it is believed that higher temperatures early during saccharification and fermentation can increase conversion of starch to fermentable sugar when ethanol concentrations are low. This can aid in increasing ethanol yield. At higher ethanol concentrations, this alcohol can adversely affect the yeast. Thus, it is believed that lower temperatures later during saccharification and fermentation are beneficial to decrease stress on the yeast. This can aid in increasing ethanol yield.

Also not limiting to the present invention, it is believed that higher temperatures early during saccharification and fermentation can reduce viscosity during at least a portion of the fermentation. This can aid in temperature control. It is also believed that lower temperatures later during saccharification and fermentation are beneficial to reduce the formation of glucose after the yeast has stopped fermenting. Glucose formation late in fermentation can be detrimental to the color of the distillers dried grain co-product.

In an embodiment, saccharification and fermentation is conducted at a pH of about 6 or less, pH of about 3 to about 6, about 3.5 to about 6, about 4 to about 5, about 4 to about 4.5, about 4.5 to about 5, or about 4.5 to about 4.8. The initial pH of the saccharification and fermentation mixture can be adjusted by addition of, for example, ammonia, sulfuric acid, phosphoric acid, process waters (e.g., stillage (backset), evaporator condensate (distillate), side stripper bottoms, and the like), and the like.

In an embodiment, saccharification and fermentation is conducted for about to 25 (e.g., 24) to about to 150 hours, about 25 (e.g., 24) to about 72 hours, about 45 to about 55 hours, about 50 (e.g., 48) to about 96 hours, about 50 to about 75 hours, or about 60 to about 70 hours. For example, saccharification and fermentation can be conducted for about 30, about 40, about 50, about 60, or about 70 hours. For example, saccharification and fermentation can be conducted for about 35, about 45, about 55, about 65, or about 75 hours.

In an embodiment, simultaneous saccharifying and fermenting can be carried out employing quantities of enzyme and yeast selected to maintain high concentrations of yeast and high levels of budding of the yeast in the fermentation broth. For example, the present process can employ quantities of enzyme and yeast selected to maintain yeast at or above about 200 cells/mL, at or above about 300 cells/mL, or at about 300 to about 600 cells/mL.

In an embodiment, simultaneous saccharifying and fermenting can be carried out employing quantities of enzyme and yeast selected for effective fermentation without added exogenous nitrogen; without added protease; and/or without added backset. Backset can be added, if desired, to consume process water and reduce the amount of wastewater produced by the process. In addition, the present process maintains low viscosity during saccharifying and fermenting.

In an embodiment, simultaneous saccharifying and fermenting can be carried out employing quantities of enzyme and yeast selected to maintain low concentrations of soluble sugar in the fermentation broth. In an embodiment, simultaneous saccharifying and fermenting can be carried out employing quantities of enzyme and yeast selected to maintain low concentrations of glucose in the fermentation broth. For example, the present process can employ quantities of enzyme and yeast selected to maintain glucose at levels at or below about 2 wt-%, at or below about 1 wt-%, at or below about 0.5 wt-%, or at or below about 0.1 wt-%. For example, the present process can employ quantities of enzyme and yeast selected to maintain glucose at levels at or below about 2 wt-% during saccharifying and fermenting. For example, the present process can employ quantities of enzyme and yeast selected to maintain glucose at levels at or below about 2 wt-% from hours 0-10 (or from 0 to about 15% of the time) of saccharifying and fermenting. For example, the present process can employ quantities of enzyme and yeast selected to maintain glucose at levels at or below about 1 wt-%, at or below about 0.5 wt-%, or at or below about 0.1 wt-% from hours 12-54 (or from about 15% to about 80% of the time) of saccharifying and fermenting. For example, the present process can employ quantities of enzyme and yeast selected to maintain glucose at levels at or below about 1 wt-% from hours 54-66 (or about from 80% to about 100% of the time) of saccharifying and fermenting.

In an embodiment, simultaneous saccharifying and fermenting can be carried out employing quantities of enzyme and yeast selected to maintain low concentrations of maltose (DP2) in the fermentation broth. For example, the present process can employ quantities of enzyme and yeast selected to maintain maltose at levels at or below about 0.5 wt-% or at or below about 0.2 wt-%.

In an embodiment, simultaneous saccharifying and fermenting can be carried out employing quantities of enzyme and yeast selected to maintain low concentrations of dextrin in the fermentation broth. For example, the present process can employ quantities of enzyme and yeast selected to maintain maltotriose (DP3) at levels at or below about 0.5 wt-%, at or below about 0.2 wt-%, or at or below about 0.1 wt-%. For example, the present process can employ quantities of enzyme and yeast selected to maintain dextrin with a degree of polymerization of 4 or more (DP4+) at levels at or below about 1 wt-% or at or below about 0.5 wt-%.

In an embodiment, simultaneous saccharifying and fermenting can be carried out employing quantities of enzyme and yeast selected to maintain low concentrations of fusel oils in the fermentation broth. For example, the present process can employ quantities of enzyme and yeast selected to maintain fusel oils at levels at or below about 0.4 to about 0.5 wt-%.

For example, simultaneous saccharifying and fermenting can employ acid fungal amylase at about 0.05 to about 10 AFAU per gram of dry solids reduced plant material (e.g., DSC) and glucoamylase at about 0.5 to about 6 AGU per gram dry solids reduced plant material (e.g., DSC). For example, simultaneous saccharifying and fermenting can employ acid fungal amylase at about 0.1 to about 10 AFAU per gram of dry solids reduced plant material (e.g., DSC) and glucoamylase at about 0.5 to about 6 AGU per gram dry solids reduced plant material (e.g., DSC). For example, simultaneous saccharifying and fermenting can employ acid fungal amylase at about 0.3 to about 3 AFAU per gram of dry solids reduced plant material (e.g., DSC) and glucoamylase at about 1 to about 3 AGU per gram dry solids reduced plant material (e.g., DSC). For example, simultaneous saccharifying and fermenting can employ acid fungal amylase at about 1 to about 2 AFAU per gram of dry solids reduced plant material (e.g., DSC) and glucoamylase at about 1 to about 1.5 AGU per gram dry solids reduced plant material (e.g., DSC).

Additional Ingredients for Saccharification and/or Fermentation

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, and the like.

Recovering Ethanol from the Beer

The product of the fermentation process is referred to herein as "beer". For example, fermenting corn produces "corn beer". Ethanol can be recovered from the fermentation mixture, from the beer, by any of a variety of known processes. For example, ethanol can be recovered by distillation.

The remaining stillage includes both liquid and solid material. The liquid and solid can be separated by, for example, centrifugation. The recovered liquid, thin stillage, can be employed as at least part of the liquid for forming the saccharification and fermentation mixture for subsequent batches or runs.

The recovered solids, distiller's dried grain, include unfermented grain solids and spent yeast solids. Thin stillage can be concentrated to a syrup, which can be added to the distiller's dried grain and the mixture then dried to form distiller's dried grain plus solubles. Distiller's dried grain and/or distiller's dried grain plus solubles can be sold as animal feed.

Burn-Out of Residual Starches for Subsequent Secondary Fermentation

In an embodiment, the present method can include heat treatment of the beer or stillage, e.g., between the beer well and distillation. In an embodiment, the present method can include heat treatment of the beer or stillage and enzyme addition, e.g., between the beer well and distillation. This heat treatment can convert starches to dextrins and sugars for subsequent fermentation in a process known as burn-out. Such a treatment step can also reduce fouling of distillation trays and evaporator heat exchange surfaces. In an embodiment, heat treatment staging can be performed on whole stillage or thin stillage. Following enzymatic treatment of the residual starches, in an embodiment, the resulting dextrins and sugars can be fermented within the main fermentation process as recycled backset or processed in a separate fermentation train to produce ethanol. In an embodiment, the liquefaction and saccharification on whole stillage or thin stillage produced by centrifugation can be accelerated after distillation.

Fractionation of Solids from Fermentation

Large pieces of germ and fiber can ferment the residual starch in the fermenter. After fermentation, the fractions could be removed prior to or after distillation. Removal can be effected with a surface skimmer before to distillation. In an embodiment, screening can be performed on the beer. The screened material can then be separated from the ethanol/water mix by, for example, centrifugation and rotary steam drum drying, which can remove the residual ethanol from the cake. In embodiments in which the larger fiber and germ pieces are removed prior to bulk beer distillation, a separate stripper column for the fiber/germ stream can be utilized. Alternatively, fiber and germ could be removed by screening the whole stillage after distillation.

In an embodiment, all the components are blended and dried together. The fiber and germ can be removed from the finished product by aspiration and/or size classification. The fiber from the DDGS can be aspirated. Removal of fiber by aspiration after drying can increase the amount of oil and protein in the residual DDGS, for example, by 0.2 to 1.9% and 0.4 to 1.4%, respectively. The amount of NDF in the residual DDGS can decrease, for example, by 0.1 to 2.8%.

In an embodiment, fractionation can employ the larger fiber and germ pieces to increase the particle size of that part of the DDGS derived from the endosperm, as well as to improve syrup carrying capacity. A ring dryer disintegrator can provide some particle size reduction and homogenization.

Methods and Systems for Drying Wet Cake to Make Distiller's Dried Grains

The beer produced by fermentation includes ethanol, other liquids, and solid material. Centrifugation and/or distillation of the beer can yield solids known as wet cake and liquids known as thin stillage. The wet cake can be dried to produce distiller's dried grain. The thin stillage can be concentrated to a syrup, which can be added to the wet cake or distiller's dried grain and the mixture then dried to form distiller's dried grain plus solubles. The present method can include drying the wet cake to produce distiller's dried grain. The present method can include drying the syrup plus distiller's dried grain to produce distiller's dried grain plus solubles. The distiller's dried grain can be produced from whole grain (e.g., corn) or from fractionated grain (e.g., corn). The present method can produce high protein distiller's dried grain and/or distiller's dried grain with improved physical characteristics. Such distiller's dried grains are described hereinbelow.

Conventional ethanol production processes employed drum dryers. Advantageously, in an embodiment, the present method and system can employ a flash or ring dryer. Flash or ring dryers have not previously been employed in processes like the present one. Configurations of flash and ring dryers are known. Briefly, a flash or ring dryer can include a vertical column through which a pre-heated air stream moves the wet cake. For example, a flash or ring dryer can include one or more inlets that provide entry of heat or heated air into the dryer. This dries the wet cake. The dried wet cake is transported to the top of a column. In a ring dryer, further drying can be accomplished by moving the wet cake through one or more rings connected to the column. For example, a ring dryer can include one or more inlets through which heated air enters a ring structure which propels or circulates the wet cake in or around the ring structure. The dried wet cake can then be pneumatically conveyed to down-stream separating equipment such as a cyclone or dust collector.

The present method can include employing a flash dryer to dry (i.e., flash drying) the wet cake and to produce distiller's dried grain. The present method can include employing a flash dryer to dry (i.e., flash drying) the syrup plus distiller's dried grain to produce distiller's dried grain plus solubles. Employing a flash dryer can produce high protein distiller's dried grain and/or distiller's dried grain with improved physical characteristics. Such distiller's dried grains are described hereinbelow.

The present method can include employing a ring dryer to dry (i.e., ring drying) the wet cake and to produce distiller's dried grain. The present method can include employing a ring dryer (i.e., ring drying) to dry the syrup plus distiller's dried grain to produce distiller's dried grain plus solubles. Employing a ring dryer can produce high protein distiller's dried grain and/or distiller's dried grain with improved physical characteristics. Such distiller's dried grains are described hereinbelow.

The present method can include employing a fluid bed dryer to dry (i.e., fluid bed drying) the wet cake and to produce distiller's dried grain. The present method can include employing a fluid bed dryer to dry (i.e., fluid bed drying) the syrup plus distiller's dried grain to produce distiller's dried grain plus solubles. Employing a fluid bed dryer can produce high protein distiller's dried grain and/or distiller's dried grain with improved physical characteristics. Such distiller's dried grains are described hereinbelow.

The present method can include adding syrup (backset or thin stillage) to the wet cake before, during, or after drying. In an embodiment, the present method includes adding syrup (backset or thin stillage) to the wet cake during drying. For example, the method can include mixing wet cake and syrup in the dryer. For example, the method can include flowing or injecting syrup into the flash, ring, or fluid bed dryer. In an embodiment, the present method includes adding syrup into the column or ring of the dryer in the presence of wet cake and/or distiller's dried grain.

Although not limiting to the present invention, it is believed that flash and/or ring dryers differ from rotary or drum dryers by providing decreased exposure of wet cake to high temperatures of the drying process. A rotary or drum dryer generally has high temperature metal that is in prolonged contact with the wet cake product. It is believed that prolonged contact of this high temperature metal with the wet cake can result in browned, burned, or denatured distiller's dried grains or distiller's dried grains plus solubles. Further, the internal air temperature can be higher in a rotary or drum dryer.

Accordingly, in an embodiment, the present method can include drying the wet cake or wet cake plus syrup for a shorter time than employed with a rotary or drum dryer, and obtaining distiller's dried grain or distiller's dried grain plus solubles that has been sufficiently dried. Accordingly, in an embodiment, the present method can include drying the wet cake or wet cake plus syrup at a lower temperature than employed with a rotary or drum dryer, and obtaining distiller's dried grain or distiller's dried grain plus solubles that has been sufficiently dried. In an embodiment, the method includes changing the drying temperature during drying.

Although not limiting to the present invention, in certain embodiments, such drying systems and methods can provide one or more advantages such as decreased energy consumption in drying, decreased leakage from the drying system.

An embodiment of this invention is the use of flash or ring dryer(s) to change the conditions inside the dryer system to increase or decrease temperature. An embodiment of this invention is the use of flash or ring dryer(s) to change the conditions inside the dryer system to increase or decrease the moisture. An embodiment of this invention is the use of flash or ring dryer(s) to change the conditions inside the dryer system to increase or decrease recycle speed. An embodiment of this invention is the use of flash or ring dryer(s) to change the conditions inside the dryer system to increase or decrease the feed rate into the dryer system.

Continuous Fermentation

The present process can be run via a batch or continuous process. A continuous process includes moving (pumping) the saccharifying and/or fermenting mixtures through a series of vessels (e.g., tanks) to provide a sufficient duration for the process. For example, a multiple stage fermentation system can be employed for a continuous process with 48-96 hours residence time. For example, reduced plant material (e.g., fractionated plant material) can be fed into the top of a first vessel for saccharifying and fermenting. Partially incubated and fermented mixture can then be drawn out of the bottom of the first vessel and fed in to the top of a second vessel, and so on.

Although not limiting to the present invention, it is believed that the present method is more suitable than conventional methods for running as a continuous process. It is believed that the present process provides reduced opportunity for growth of contaminating organisms in a continuous process. At present, the majority of dry grind ethanol facilities employ batch fermentation technology. This is in part due to the difficulty of preventing losses due to contamination in these conventional processes. For efficient continuous fermentation using traditional liquefaction technology, the conventional belief is that a separate saccharification stage prior to fermentation is necessary to pre-saccharify the mash for fermentation. Such pre-saccharification insures that there is adequate fermentable glucose for the continuous fermentation process.

The present method achieves efficient production of high concentrations of ethanol without a liquefaction or saccharification stage prior to fermentation. This is surprising since this conventional wisdom teaches that it is necessary to have adequate levels of fermentable sugar available during the fermentation process when practiced in a continuous mode. In contrast the present method can provide low concentrations of glucose and efficient fermentation. In the present method, it appears that the glucose is consumed rapidly by the fermenting yeast cell. It is believed that such low glucose levels reduce stress on the yeast, such as stress caused by osmotic inhibition and bacterial contamination pressures. According to the present invention, ethanol levels greater than 18% by volume can be achieved in about 45 to about 96 hours.

Endosperm, Fiber, and Germ Fermentation

In an embodiment, the present process can ferment a portion of a reduced plant material, such as corn. For example, the process can ferment at least one of endosperm, fiber, or germ. The present process can increase ethanol production from such a portion of corn. In an embodiment, the present process can saccharify and ferment endosperm. Endosperm fermentation is lower in free amino nitrogen (FAN) towards the beginning of fermentation due to the removal of germ, which contains FAN. The present process can, for example, preserve the FAN quality of the endosperm compared to conventional high temperature liquefaction. An embodiment of the present invention includes the use of endosperm FAN, which can increase flexibility and efficiency of fermentation.

In an embodiment, the present process can employ endogenous enzyme activity in the grain. In an embodiment, dramatic increase in FAN in whole corn and defibered corn fermentations are reached compared to the initial mash slurry.

Conventional grain dry milling operations separate germ (containing oil) and bran or pericarp (fiber fraction) from the endosperm (starch and protein) portion of the grain using a series of steps and procedures. These steps and procedures include: grain cleaning, tempering, degerming, particle size reduction, roller milling, aspirating, and sifting. This process differs from the traditional wet milling of grains (commonly corn) which are more expensive and water intensive, but capable of achieving cleaner separations of the components of the grain. Dry milling processes offer a version of separating components using lower capital costs for facilities. Also, these processes require less water for operation. The tempering process in dry milling requires less water than required in wet milling.

The competitiveness of dry grain fractionation processes is enhanced when the process of the present invention is utilized for ethanol conversion of these fractions. Traditionally dry milling processes produce various grades of each fraction (germ, bran, and endosperm). In an embodiment, the present method provides bran and endosperm fractions that can be more readily fermented. Depending on the desired purity of each fraction, the fractions can either be pooled to create composites of each stream, or the fractions can be processed individually.

Yeast uses FAN in the present process. In the conventional liquefaction process, FAN levels fall throughout fermentation as yeast cells assimilate and metabolize available FAN during the course of fermentation. Toward the end of fermentation in the conventional process, FAN levels rise illustrating the liberation of cellular FAN coinciding with death and lysis of yeast cells. In contrast, FAN utilization kinetics in the raw starch process is more rapid. FAN levels reach a minimum at least 24 hours earlier, and then begin increasing dramatically. Some of the increase of FAN is due to yeast cell death resulting from the accelerated fermentation.

High Alcohol Beer

The present invention also relates to a high alcohol beer. In an embodiment, the process of the present invention produces beer containing greater than 18 vol-% ethanol. The present process can produce such a high alcohol beer in about 40 to about 96 hours or about 45 to about 96 hours. In an embodiment, the beer includes 18 vol-% to about 23 vol-% ethanol. For example, the present method can produce alcohol contents in the fermenter of 18 to 23% by volume in about 45 to 96 hours.

By way of further example, the present method can produce alcohol content in the fermenter of 18 to 23% by volume in about 45 to 96 hours. In certain embodiments, the majority of the alcohol (80% or more of the final concentration) is produced in the first 45 hours. Then, an additional 2 to 5 vol-% alcohol can be produced in the final 12-48 hours. Concentrations of ethanol up to 23 vol-% can be achieved with fermentation time up to 96 hours. It can be economically advantageous to harvest after 48 to 72 hours of fermentation to increase fermenter productivity.

The present beer can include this high level of ethanol even when it includes high levels of residual starch. For example, the present beer can include ethanol at 18 to 23 vol-% when it contains 0 to 30% residual starch. The present beer can contain residual starches as low as 0% to as high as 20% residual starch.

By conventional measures, high levels of residual starch indicate inefficient fermentation, which yields only low levels of ethanol. In contrast, although not limiting to the present invention, it is believed that the present method results in fewer Maillard type reaction products and more efficient yeast fermentation (e.g., reduced levels of secondary metabolites). This is believed to be due to the low glucose levels and low temperatures of the present method compared to conventional saccharification and liquefaction. Thus, the present method can produce more alcohol even with higher levels of residual starch.

In an embodiment, the present beer includes fewer residual byproducts than conventional beers, even though residual starch can be higher. For example, residual glucose, maltose, and higher dextrins (DP3+) can be as much as 0.8 wt-% lower than in conventional beers produced under similar fermentation conditions. By way of further example, residual glycerol can be as much as 0.7 wt-% less. Lactic acid and fusel oils can also be significantly reduced. For example, the present beer can include less than or equal to about 0.2 wt-% glucose, about 0.4 wt-%, about 0.1 wt-% DP3, undetectable DP4+, 0.7 wt-% glycerol, about 0.01 wt-% lactic acid, and/or about 0.4 wt-% fusel oils.

Distiller's Dried Grain

High Protein Distiller's Dried Grain

The present invention also relates to a distiller's dried grain product. The distiller's dried grain can also include elevated levels of one or more of protein, fat, fiber (e.g., neutral detergent fiber (NDF)), and starch. For example, the present distiller's dried grain can include 34 or more wt-% protein, about 25 to about 60 wt-% protein, about 25 to about 50 wt-% protein, or about 30 to about 45 wt-% protein. In certain circumstances the amount of protein is about 1 to about 2 wt-% more protein than produced by the conventional process. For example, the distiller's dried grain can include 15 or more wt-% fat, about 13 to about 17 wt-% fat, or about 1 to about 6 wt-% more fat than produced by the conventional process. For example, the distiller's dried grain can include 31 or more wt-% fiber, about 23 to about 37 wt-% fiber, or about 3 to about 13 wt-% more fiber than produced by the conventional process. For example, the distiller's dried grain can include 12 or more wt-% starch, about 1 to about 23 wt-% starch, or about 1 to about 18 wt-% more starch than produced by the conventional process.

In an embodiment, the present distiller's dried grain includes elevated levels of B vitamins, vitamin C, vitamin E, folic acid, and/or vitamin A, compared to conventional distiller's dried grain products. The present distiller's dried grain has a richer gold color compared to conventional distiller's dried grain products.

Distiller's Dried Grain with Improved Physical Characteristics

The present invention also relates to a distiller's dried grain with one or more improved physical characteristics, such as decreased caking or compaction or increased ability to flow. The present process can produce such an improved distiller's dried grain.

Although not limiting to the present invention, it is believed that the present process can produce fermentation solids including higher molecular weight forms of carbohydrates. Such fermentation solids can, it is believed, exhibit a higher glass transition temperature (i.e. higher $T_g$ values) compared to solids from the conventional process. For example, residual starches can have a high $T_g$ value. Thus, through control of starch content in the DDG and DDGS, the present process can manufacture DDG or DDGS with target $T_g$ values.

Further, according to the present invention, adding an alkaline syrup blend (e.g., syrup plus added lime or other alkaline material) to the fermentation solids (e.g., distiller's dried grains) can provide decreased caking or compaction or increase ability to flow to the distiller's dried grain with solubles (DDGS).

Although not limiting to the present invention, it is believed that organic acids such as lactic, acetic, and succinic acids which are produced in fermentation have a lower $T_g$ value than their corresponding calcium salts. Maintenance of residual carbohydrate in higher molecular weight form, or addition of lime to form calcium salts of organic acids, are two strategies for forming higher $T_g$ value co-products that will be less likely to undergo the glass transition, resulting in the deleterious phenomenon known as caking.

In an embodiment, DDG or DDGS of or produced by the method of the present invention flows more readily than DDG or DDGS produced by the conventional process.

Although not limiting to the present invention, it is believed that process of the present invention can need not destroy protein in the fermented plant material (e.g., fractionated plant material). Corn contains prolamins, such as zein. Grain sorghum, for example, contains a class of zein-like proteins known as kafirins, which resemble zein in amino acid composition. The thermal degradation that occurs during liquefaction, distillation, and high temperature drying produces DDG and DDGS including significant amounts of degraded protein. It is believed that the process of the present invention can provides improved levels of the prolamin fraction of cereal grains.

It is believed that extended exposure to high alcohol concentrations that can be achieved by the present process can condition the proteins in the plant material (e.g., fractionated plant material). This can solubilize some of the proteins. For example, it is believed that in distillation the ethanol concentration reaches levels that can solubilize prolamins (e.g., zein) in the beer. Upon the removal, or "stripping," of ethanol from the beer, prolamins (such as zein) can be recovered in concentrated form in DDG and DDGS. The resulting high protein content of DDG and DDGS can be advantageous for various end uses of DDG and DDGS, for example in further processing or compounding.

In an embodiment, efficient fermentation of the present process removes from the DDG or DDGS non zein components such as starch. Fractionating the plant material, e.g., corn, can also increase levels of proteins, such as zein, in the DDG or DDGS. For example, removing the bran and germ fractions prior to fermentation can concentrate zein in the substrate. Zein in corn is isolated in the endosperm. Fermentation of zein enriched endosperm results in concentration of the zein in the residuals from fermentation.

In an embodiment, the present method can operate on fractionated plant material (such as endosperm, fiber, other parts of cereal grain) to provide a protein enriched solid product from fermentation. For example, the present method operated on fractionated plant material can produce a DDG enriched in prolamin, such as zein.

In an embodiment, the process of the present invention can provide DDG and DDGS with different, predetermined $T_g$ values. The process of the present invention can ferment fractions containing high, medium, or low levels of zein, thus varying the glass transition temperature of the resulting DDG or DDGS. The resulting co-product $T_g$ can be directly proportional to the prolamin protein (such as zein) content. The process of the current invention is desirable for the fermentation of high protein corn. This also allows production of DDG and DDGS with a higher prolamin (zein) content.

Residual starch remaining at the end of fermentation preferentially segregates into the thin stillage fraction, which is subsequently evaporated to produce syrup. The wet cake fraction produced by the present method, which can be dried separately to produce DDG, can be higher in prolamin protein (such as zein) than conventional DDG. The present process allows syrup and wet cake blend ratios to be varied. This results in DDG/DDGS with varying ratios of prolamin protein (such as zein) and residual starch. As the residual starch in the wet cake reduces the protein in the wet cake increases. This indicates an inverse relationship. A similar response occurs in the syrup fraction.

It is believed that starch can segregate into the liquid fraction. The amount of starch in the DDGS can be varied by blending syrup at rates ranging from 0 lbs. dry weight of syrup solids to 1.2 lbs. of syrup solids per lb. of wet cake solids before, and various times during drying to create the final DDGS product. The disproportionate segregation of residual starches into the backset or thin stillage fraction can provide both the aforementioned burn-out and secondary fermentation to be performed on these fractions. Since the thin stillage is evaporated to produce syrup, the centrifuge mass balance also enables DDGS production at various $T_g$ values depending on the desired properties and their dependence on $T_g$.

Emissions

The present invention has emissions benefits. Emissions benefits result in the reduction in byproducts created in the ethanol manufacturing process. There is a marked reduction in extraction of fats and oils in the mash from the germ fraction of cereal grains. There is a reduction of byproducts from Maillard reactions typically formed during cooking and liquefaction. And there is a reduction in fermentation byproducts. These observations result in reduced emissions during the recovery of co-products. The concentration and emission rates of volatile organic compounds (VOC), carbon monoxide (CO), nitric oxide compounds (NOx), sulfur oxides (SO2), and other emissions are considerably lower. See Table 1. Note that other manufacturers have attempted to lower emissions by manufacturing wet cake instead of drying to DDG or DDGS.

The present invention also relates to volatile organic compounds (VOC), such as those produced by drying products of a fermentation process. The present method includes producing ethanol, distiller's dried grain, and additional useful fermentation products with production of lower levels of VOC compared to conventional processes. For example, in the present method, drying distillation products (e.g., spent grain) produces reduced levels of VOC.

Conventional fermentation processes using corn, for example, produces about 2.1 pounds of VOC's from drying distillation products from each ton of corn processed. The actual stack emissions can be less due to pollution control equipment. The present method results in at least 30% reduction in VOC production to about 1.47 or less pounds per ton of corn processed. These emissions reductions are unexpected yet highly significant, and provide for more efficient use of emissions reduction control technology, such as thermal oxidizers.

VOC produced by fermentation processes include ethanol, acetic acid, formaldehyde, methanol, acetaldehyde, acrolein, furfural, lactic acid, formic acid, and glycerol.

The present invention also relates to carbon monoxide (CO), such as those produced by drying products of a fermentation process. The present method includes producing ethanol, distiller's dried grain, and additional useful fermentation products with production of lower levels of CO compared to conventional processes. For example, in the present method, drying distillation products (e.g., spent grain) produces reduced levels of CO.

Conventional fermentation processes using corn, for example, produces about 1.4 pounds of CO's from drying distillation products from each ton of corn processed. The actual stack emissions can be less due to pollution control equipment. The present method results in a 30% reduction in CO production to about 0.98 or less pounds per ton of corn processed. These emissions reductions are unexpected yet highly significant, and provide for more efficient use of emissions reduction control technology, such as thermal oxidizers.

TABLE 1

Emissions Reductions

| Emission Type | | Units | Conventional Run | Inventive Process | Emissions Reduction % |
|---|---|---|---|---|---|
| VOC | Concentration | ppmv lb/dscf | 663 | 459.65 | 30.67 |
| | Emission Rate | lb/hr | 13.35 | 7.91 | 40.75 |
| CO | Concentration | ppmv lb/dscf | 434 | 234.13 | 46.05 |
| | Emission Rate | lb/hr | 9.1 | 4.94 | 45.71 |

System for Producing Ethanol

In an embodiment, the invention relates to a system that produces ethanol. The present system can include a saccharification apparatus 1, a fermentation apparatus 2, a distillation apparatus 3, and a dryer apparatus 4.

The saccharification apparatus 1 can be any of a variety of apparatus suitable for containing or conducting saccharification. The saccharification apparatus 1 can be, for example, a vessel in which reduced plant material can be converted to a sugar, which can be fermented by a microorganism such as yeast. The saccharification apparatus 1 can be configured to maintain a saccharification mixture under conditions suitable for saccharification. The saccharification apparatus 1 can be configured to provide for the conversion of reduced plant material with the addition of enzymes. In an embodiment, the saccharification apparatus 1 is configured for mixing reduced plant material with a liquid and adding a saccharifying enzyme composition to the liquid. In an embodiment, the saccharification apparatus 1 is configured for saccharification at a variety of pHs and temperatures, but preferably at a pH of 6.0 or less, and at a temperature of about 25 to about 40° C.

The fermentation apparatus 2 can be any of a variety of apparatus suitable for containing or conducting fermentation. The saccharification apparatus 1 can be, for example, a vessel in which sugar from reduced plant material can be fermented to ethanol. The fermentation apparatus 2 can be configured to maintain a fermentation mixture under conditions suitable for fermentation. In an embodiment, the fermentation apparatus 2 can be configured for fermenting through use of a microorganism, such as yeast. In an embodiment, the fermentation apparatus 2 can be configured to ferment a starch composition that has not been cooked, specifically the saccharification mixture. In an embodiment, the apparatus can employ any variety of yeasts that yields a commercially significant quantity of ethanol in a suitable time. Yeast can be added to the apparatus by any of a variety of methods known for adding yeast to a system that conducts fermentation. The fermentation apparatus 2 can be configured for fermentation for about 25 to 150 hours at a temperature of about 25 to about 40 degrees C.

The saccharification apparatus 1 and the fermentation apparatus 2 can be a single, integrated apparatus. In an embodiment, this apparatus is configured to provide higher temperatures early on during simultaneous conversion of reduced plant material to sugars and fermentation of those sugars. In an embodiment, this apparatus is configured to provide lower temperatures later during the simultaneous saccharification and fermentation. The apparatus also may utilize the reagents and conditions described above for saccharification and fermentation, including enzymes and yeast.

The distillation apparatus 3 can be any of a variety of apparatus suitable for distilling products of fermentation. The distillation apparatus 3 can be, for example, configured to recover ethanol from the fermentation mixture ("beer"). In an embodiment, the fermentation mixture is treated with heat prior to entering the distillation apparatus 3. In another embodiment, fractions of large pieces of germ and fiber are removed with a surface skimmer or screen prior to or after entering the distillation apparatus 3.

The dryer apparatus 4 can be any of a variety of apparatus suitable for drying solids remaining after distillation (and optional centrifugation, for example, in a centrifuge system). In an embodiment, the dryer apparatus 4 is configured to dry recovered solids, which can result in production of distiller's dried grain. After the distillation system separates the ethanol from the beer, recovered solids remain. These recovered solids can then be dried in the dryer apparatus 4. This produces distiller's dried grain and/or distiller's dried grain plus solubles. In an embodiment, the dryer apparatus 4 can be or include a ring dryer. In an embodiment, the dryer apparatus 4 can be or include a flash dryer. In an embodiment, the dryer apparatus 4 can be or include a fluid bed dryer.

The present invention may be better understood with reference to the following examples. These examples are intended to be representative of specific embodiments of the invention, and are not intended as limiting the scope of the invention.

EXAMPLES

Example 1

The Present Process Provides Improved Efficiency with Substrates Derived from Grain Dry Milling Operations (Endosperm, Fiber, & Germ)

The present invention provides an improved method for fermenting substrates derived from grain milling (dry fractionation) processes. The present process is useful for endosperm fermentation since FAN levels in the mash are reduced to the removal of germ. The present process contributes to the endogenous enzymes activity in the grain. Dramatic increase in FAN in whole corn and defibered corn fermentations are reached compared to the initial mash slurry.

Results and Discussion

Figure 2A:
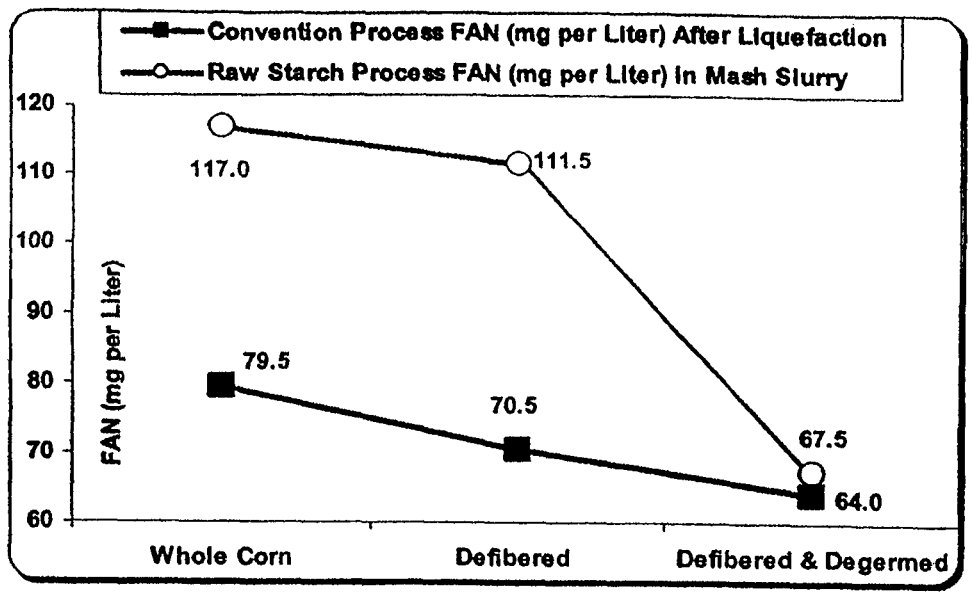
FIGS. 2A through 2C schematically illustrate that the present process provides improved efficiency for fermentation of corn fractions produced by dry milling fractionation processes.
Figure 2B:
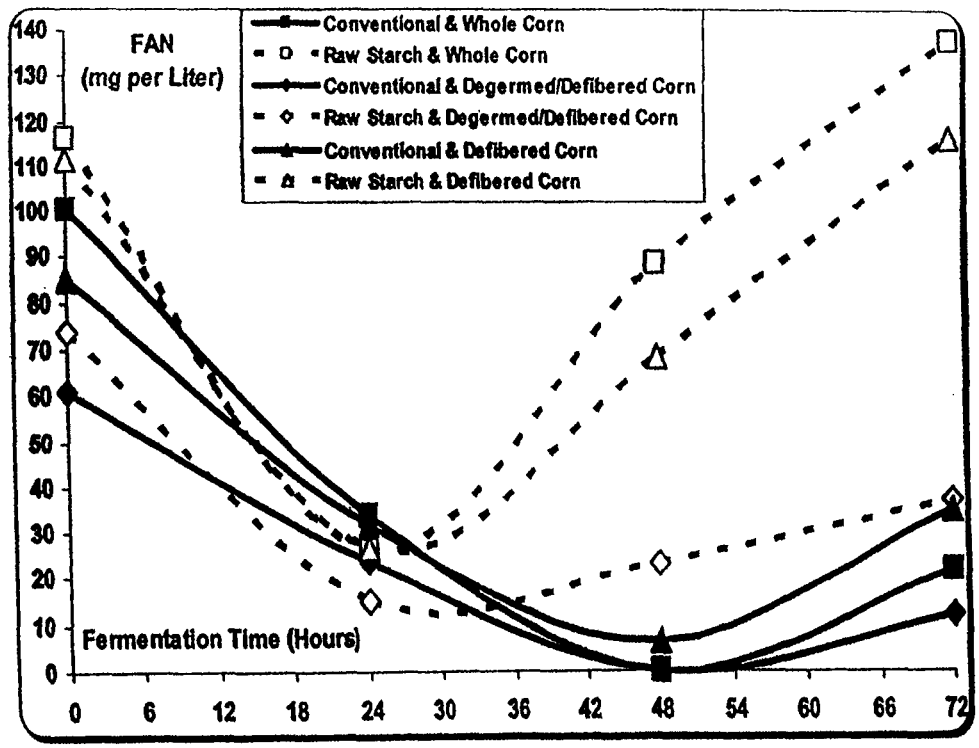

The present process is useful for endosperm fermentation since FAN levels in the mash are reduced due to the removal of germ, as shown in FIG. 2A. FAN supplies necessary nitrogen for yeast growth and reducing ethanol related stress in high gravity ethanol fermentations. FIG. 2A also reveals the negative impact of liquefaction on reducing the amount of FAN available in fermentation. The generation of dextrins and soluble sugars during the high temperature liquefaction results in Maillard condensation reactions between carbonyl groups on sugars and amino groups on amino acids and peptides. This results in a loss in potential yield (due to unavailable carbohydrate) as well as a reduction in the nutritional quality of the mash for sustaining efficient high gravity fermentation (due to reduction in FAN). The present process also enables the endogenous enzyme activity in the grain to contribute to the generation of soluble sugars and amino nitrogen in the mash. These beneficial activities are lost during the conventional liquefaction stage. The kinetics of FAN utilization is illustrated in FIG. 2B for fermentation of various dry milled grain fractions.

It is interesting to note that FAN kinetics in the conventional process all follow a similar utilization pathway for each corn fraction. During the first half of fermentation, FAN is consumed in the course of yeast growth. Later, FAN levels are observed to increase, presumably due the liberation of cellular FAN corresponding to yeast cell death and lysis. Initial FAN utilization in the raw starch process is observed to be much more rapid. Also note the dramatic increase in FAN at the end of raw starch fermentations. This increase in FAN could be the result of yeast cell death since the rate of ethanol production is much faster in raw starch fermentations. It could also be due to generation of FAN from endogenous enzymes in the grain. Note that when germ is removed, there is less of an increase in FAN during the latter half of the fermentation. These observations suggest an additional aspect of the raw starch process.

Figure 2C:
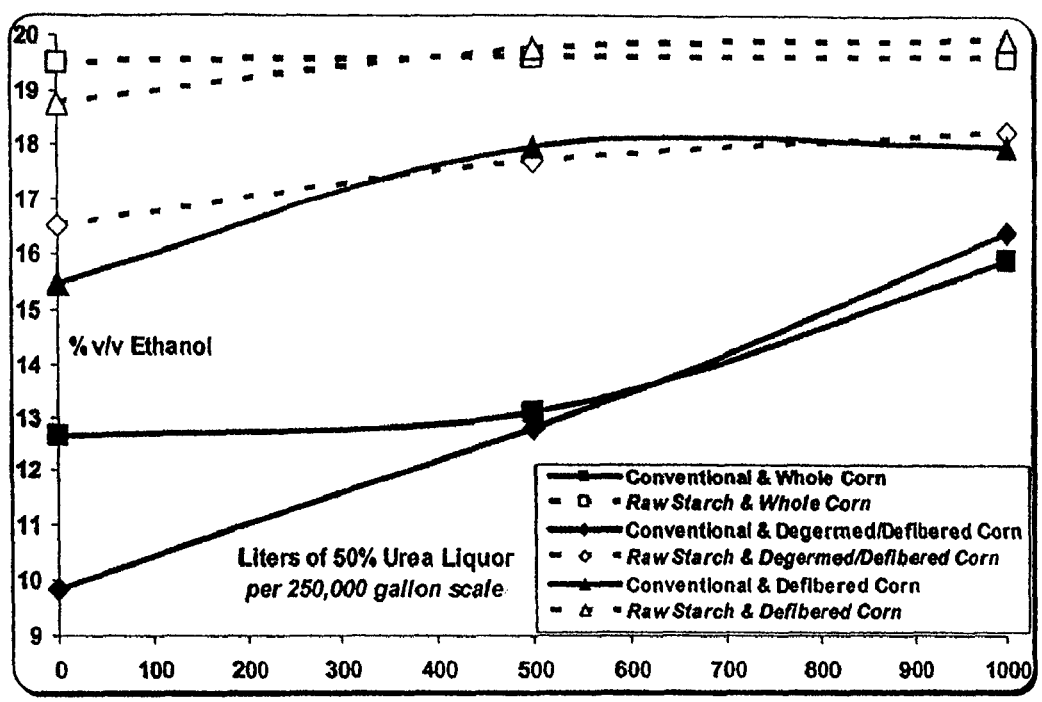

FIG. 2C illustrates the impact of FAN on corn fraction fermentations run in the absence of backset, comparing and contrasting the sensitivity of the two processes to additional FAN addition. It is apparent that the process of the present invention significantly improves the potential substrate quality from a dry milling fractionation facility for fermentation, reducing the importance of additional FAN. The present process is superior to the conventional liquefaction process, since the conventional liquefaction process is more sensitive to disruptive impact of substrate quality as measured by FAN levels.

Example 2

The Present Method Produced High Protein DDG From Fractionated Plant Product

The present invention demonstrated that fractionation of corn prior to fermentation provides high levels of protein in the resulting DDG.

Materials and Methods

Corn was fractionated prior to fermentation through use of a Satake fractionation system. After fractionation, the corn was fermented according to the present invention employing for saccharification glucoamylase and acid fungal amylase without cooking. The fermentation was conducted at 90° F. and at a pH of 5. After the corn solids were fermented, the ethanol was distilled out. The remaining solids were then dried, and samples of fiber, germ, and starch were taken. All fractionation samples were ground for twenty seconds on a Knifetec. These samples were then analyzed for starch, protein, fat, and neutral detergent fiber content. The percent ethanol yield was also calculated for each sample. See also the Materials and Methods sections for the other examples for additional information about how these experiments were conducted.

Results and Discussion

The present method produced high protein DDG and high levels of ethanol compared to a conventional process (Table 2). Table 2 shows results for ethanol and DDG produced from two representative samples of each of fiber, starch, and germ samples. Fermentations B and C, the representative starch samples, resulted in the highest yield of ethanol and produced DDG with the largest percentage of protein (Table 2). The two germ samples generated the lowest yield of ethanol and the highest percentage of fat (Table 2). The fiber samples produced the lowest amount of protein (Table 2). In general, this table illustrates that fractionation increased the rate of protein retention throughout the fermentation and distillation process (Table 2).

TABLE 2

Ethanol and DDG Proximate Levels Produced From Corn Fractions

| Fermen-<br>tation | Ethanol<br>vol-% | Starch %<br>dw | Protein %<br>dw | Fat %<br>dw | NDR %<br>dw | Sample<br>Type |
|---|---|---|---|---|---|---|
| A | 8.10 | 0.00 | 22.51 | 17.93 | 30.90 | Fiber |
| B | 12.11 | 3.58 | 42.46 | 5.66 | 12.99 | Starch |
| C | 11.75 | 0.55 | 43.83 | 7.73 | 13.84 | Starch |
| D | 6.39 | 0.57 | 26.18 | 26.81 | 13.33 | Germ |
| E | 6.58 | 0.00 | 18.31 | 14.43 | 42.34 | Fiber |
| F | 4.68 | 0.34 | 22.70 | 29.49 | 17.63 | Germ |

Example 3

The Present Process Provided Improved Corn Fiber Fermentation

The present invention provides an improved method for fermenting corn fiber substrates derived from grain milling (dry fractionation) processes. The present process was useful for gentler removal of starch from corn fiber fractions via fermentation. Typically, corn fiber fractions contain recalcitrant starch deposits. The present method provided improved access to the starch present in the corn fiber.

Materials and Methods

Final fiber obtained from Broin Enterprises, Inc. (BEI) in Scotland, S. Dak. U.S.A. was used in this experiment. The makeup water used was deionized water. The 550,000 gallon fermenters were pH adjusted to 4.5 with sulfuric acid (0.5 ml of 10× solution required). The wet fiber was ground in the Knifetech mill two times for ten seconds. A 20,000 gallon yeast propagator temperature was maintained at ninety degrees Fahrenheit (90° F.) with a propagator time of eight (8) hours and pH adjusted to 5.0 with sulfuric acid. Fali yeast, obtained from Fleischmann's Yeast, was prepared using makeup water from plant operations. A commercially available glucoamylase with a dosage of 400 L was used.

Results and Discussion

TABLE 3

| GA (L) | Temp.<br>(° F.) | 0 hrs. (%<br>EtOH) | 16 hrs. (%<br>EtOH) | 24 hrs. (%<br>EtOH) | 40 hrs. (%<br>EtOH) |
|---|---|---|---|---|---|
| 400 | 98 | 0 | 4.685 | 6.141 | 7.328 |
| 400 | 95 | 0 | 4.349 | 5.649 | 6.961 |
| 400 | 101 | 0 | 4.897 | 6.351 | 7.265 |
| 400 | 104 | 0 | 5.005 | 6.419 | 7.565 |

The present process provided effective corn fiber fermentation (Table 3). The data in Table 3 indicate the positive impact of fiber fermentation as measured by ethanol yield using the present method. Varying the temperature displays the effect on ethanol recovery, with efficient ethanol recovery produced at lower temperatures. The present method effectively fermented a corn fiber fraction that in a conventional process typically stalls fermentation.

Example 4

The Present Process Provided Improved Ethanol Kinetics in Endosperm Fermentation Via Additional Germ or Germ Meal The present invention provides an improved method for fermenting fractionated grain, such as fractionated corn derived from a grain milling (dry fractionation) process.

Materials and Methods

Cook Standard Ingredients at Plant Equivalent Dose (Lab Dose) of 308 L Liquizyme SC AA (0.30 ml of a 25×) was used. Fermentation standard ingredients at plant equivalent dose (lab dose) to include 660 L Spirizyme Plus glucoamylase (0.25 ml of a 10×), 33 L protease (0.13 ml of a 100×), 4.4 lbs Lactrol (0.16 ml of a 2,000×), and no urea liquor. Fermentation temperature staging conditions included 90° F. from 0-24 hours, 84° F. from 24-48 hours, and 82° F. from 48-65 hours. Yeast propagator standard ingredients at laboratory dose to include 230 mL deionized water, 100 mL backset, 70 grams maltodextrin MO40, 0.44 mL of a 5×, 1.76 mL of a 100×, 1.07 grams, 1.07 grams, 1.70 mL of a 1000×, 0.13 grams zinc sulfate, 0.48 grams Fali Yeast for an eight (8) hour propagation, propagation temperature of ninety degrees (90° F.), with a 2.88 mL transfer of yeast propagator to each fermenter for inoculation.

Plant scale dosages refer to 550,000 gallon fermenters with 80 mL lab fermenters used. The grams of flour used and the makeup water added was adjusted for each fermenter to keep the starch content consistent. The pH of all fermenters was adjusted to 6.0 with sulfuric acid. All endosperm flour used was collected from BEI already ground, and all germ flour was ground in the KnifeTech mill (3×10 sec). The whole corn used as control was ground through a Lab 1.0 mm Screen. The pH of all drop samples was adjusted to less than 3.50 with sulfuric acid to deactivate residual enzyme activity prior to drying samples for proximate analysis.

Results and Discussion

Figure 3A:
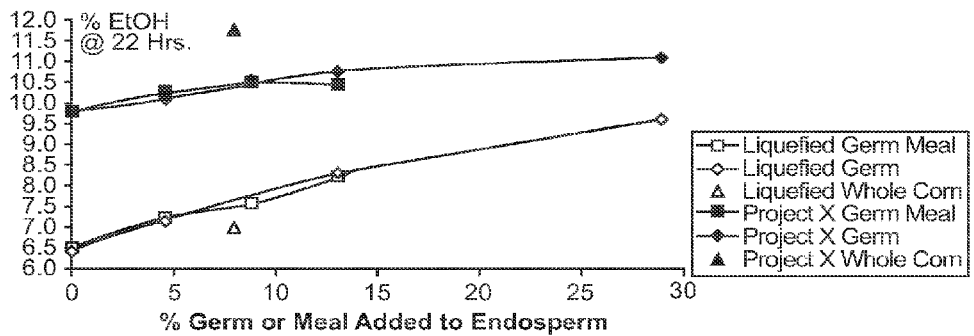
FIGS. 3A through 3C schematically illustrate that the present process provides improved efficiency for fermentation of corn fractions produced by dry milling fractionation processes.
Figure 3B:
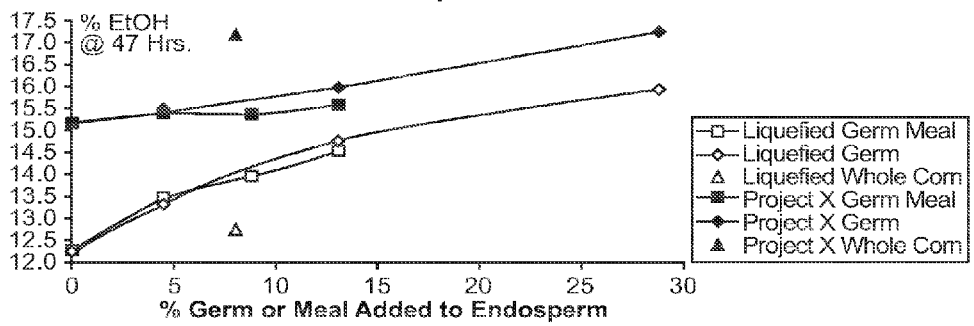
Figure 3C:
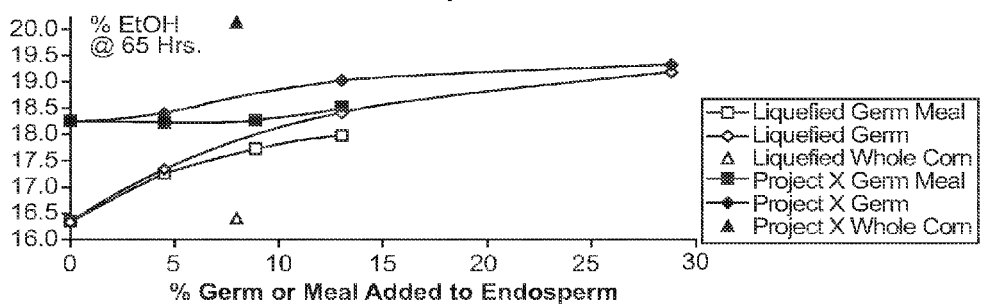

At the start of fermentation there was a measured difference in the ethanol percentage in the germ produced according to the present method compared to the liquefied germ. This difference continued throughout forty-seven hours of fermentation. A similar trend was observed between the present invention germ meal and the liquefied germ meal. The present process provided improved ethanol kinetics in endosperm fermentation via additional germ or germ meal. These results are illustrated in FIGS. 3A, 3B, and 3C.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A fermentation method comprising
    dry fractionating plant material comprising endosperm
        into components including fiber, germ and endosperm;

separating the germ and fiber components of the fractionated plant material to form a remaining portion which includes the endosperm;

reducing the size of particles in the remaining portion to form a reduced portion, wherein more than 50% of the particles fit through a sieve with a 0.5 mm mesh; and fermenting the reduced portion in a reaction mixture under acidic conditions to form a liquid comprising ethanol and a solid material, wherein the reaction mixture comprises acid stable fungal alpha amylase and yeast.

2. The method of claim 1, wherein the plant material is corn.

3. The method of claim 1, wherein the amount of said acid stable fungal alpha amylase to dry solids in said reduced portion ranges from about 0.1 to about 10 acid stable fungal alpha amylase units per gram of dry solids.

4. The method of claim 1, wherein the reaction mixture further comprises glucoamylase.

5. The method of claim 4, wherein the amount of said glucoamylase to dry solids in said reduced portion ranges from about 0.5 to about 6 glucoamylase units per gram of said dry solids.

6. The method of claim 1, wherein the acidic conditions comprise a pH of about 3 to about 6.

7. The method of claim 6, wherein the acidic conditions comprise a pH of about 4 to about 5.

8. The method of claim 1, wherein the fermentation is carried out at a temperature of about 25° C. to about 40° C.

9. A method of producing distiller's dried grains (DDG) and/or distiller's dried grains plus solubles (DDGS), the method comprising:

dry fractionating plant material comprising endosperm into components including fiber, germ and endosperm;

separating the germ and fiber components of the fractionated plant material to form a remaining portion which includes the endosperm;

reducing the size of particles in the remaining portion to form a reduced portion, wherein more than 50% of the particles fit through a sieve with a 0.5 mm mesh;

fermenting the reduced portion in a reaction mixture under acidic conditions to form a liquid comprising ethanol and a solid material, wherein the reaction mixture comprises acid stable fungal alpha amylase and yeast; and removing the liquid comprising ethanol and drying the solid material to produce distiller's dried grains and/or distiller's dried grains plus solubles.

10. The method of claim 9, wherein drying the solid material is achieved with a flash or a ring dryer.

11. The method of claim 9, wherein the plant material is corn.

12. The method of claim 9, wherein the amount of said acid stable fungal alpha amylase to dry solids in said reduced portion ranges from about 0.1 to about 10 acid stable fungal alpha amylase units per gram of dry solids.

13. The method of claim 9, wherein the reaction mixture further comprises glucoamylase.

14. The method of claim 13, wherein the amount of said glucoamylase to dry solids in said reduced portion ranges from about 0.5 to about 6 glucoamylase units per gram of said dry solids.

15. The method of claim 9, wherein the acidic conditions include a pH of about 3 to about 6.

16. The method of claim 15, wherein the acidic conditions include a pH of about 4 to about 5.

17. The method of claim 9, wherein the fermentation is carried out at a temperature of about 25° C. to about 40° C.

* * * * *